(12) United States Patent
Itoh

(10) Patent No.: US 7,889,358 B2
(45) Date of Patent: Feb. 15, 2011

(54) COLOR FILTER INSPECTION METHOD, COLOR FILTER MANUFACTURING METHOD, AND COLOR FILTER INSPECTION APPARATUS

(75) Inventor: Kenji Itoh, Hirakata (JP)

(73) Assignee: Sharp Kabushiki Kaisha, Osaka (JP)

( * ) Notice: Subject to any disclaimer, the term of this patent is extended or adjusted under 35 U.S.C. 154(b) by 225 days.

(21) Appl. No.: 12/226,681

(22) PCT Filed: Apr. 26, 2007

(86) PCT No.: PCT/JP2007/059120

§ 371 (c)(1), (2), (4) Date: Oct. 24, 2008

(87) PCT Pub. No.: WO2007/126027

PCT Pub. Date: Nov. 8, 2007

(65) Prior Publication Data

US 2009/0091768 A1    Apr. 9, 2009

(30) Foreign Application Priority Data

Apr. 26, 2006  (JP) ............................... 2006-122505

(51) Int. Cl.
*G01B 11/28* (2006.01)
(52) U.S. Cl. .................. 356/630; 356/600; 356/601
(58) Field of Classification Search ................. 356/234, 356/432, 445, 448, 600, 630
See application file for complete search history.

(56) References Cited

U.S. PATENT DOCUMENTS 4,954,723 A * 9/1990 Takahashi et al. ...... 250/559.18
5,991,038 A * 11/1999 Yamamoto .................. 356/600

(Continued)

FOREIGN PATENT DOCUMENTS

JP    03-289544    12/1991

(Continued)

OTHER PUBLICATIONS

International Search Report, Jun. 19, 2007, issued in PCT/JP2007/059120.

*Primary Examiner*—Tarifur Chowdhury
*Assistant Examiner*—Tara S Pajoohi
(74) *Attorney, Agent, or Firm*—Edwards Angell Palmer & Dodge LLP; David G. Conlin; Catherine J. Toppin

(57) ABSTRACT

Included are an illumination lamp (2) for illuminating a color filter edge (23) at a predetermined angle of incidence, a sensor (3) for taking at least two images by imaging light reflected at a predetermined angle different from the angle of incidence, an image processing section (9) for calculating a difference in luminance within a color filter in accordance with the images thus taken, and a defect determination section (13) for determining the existence of unevenness in the color filter from the difference in luminance. Provided thereby are a color filter inspection method and a color filter inspection apparatus, each for early discovering unevenness through macroscopic observation of the whole color filter by illuminating the color filter edge and by taking reflected light that is not specular reflected light, the unevenness occurring in a drying step, the color filter edge containing a boundary between a pixel and a black matrix. Further provided is a method for manufacturing a color filter with use of the color filter inspection method.

11 Claims, 12 Drawing Sheets

U.S. PATENT DOCUMENTS

| | | |
|---|---|---|
| 2009/0034827 A1 | 2/2009 | Iden |
| 2009/0046113 A1 | 2/2009 | Murakami et al. |
| 2009/0177428 A1 | 7/2009 | Iden |
| 2009/0303468 A1 | 12/2009 | Itoh et al. |

FOREIGN PATENT DOCUMENTS

| | | |
|---|---|---|
| JP | 05-302820 | 11/1993 |
| JP | 6221838 A | 8/1994 |
| JP | 07-020065 | 1/1995 |
| JP | 07-208959 A | 8/1995 |
| JP | 08-122266 A | 5/1996 |
| JP | 08-128965 A | 5/1996 |
| JP | 08-178797 | 7/1996 |
| JP | 09-068502 A | 3/1997 |
| JP | 09-072824 | 3/1997 |
| JP | 09-126891 | 5/1997 |
| JP | 10-078307 | 3/1998 |
| JP | 11-194096 | 7/1999 |
| JP | 2000-111492 | 4/2000 |
| JP | 2000-121323 | 4/2000 |
| JP | 2001-183306 | 7/2001 |
| JP | 2001-228052 | 8/2001 |
| JP | 2001-356209 | 12/2001 |
| JP | 2002-219810 | 8/2002 |
| JP | 2002-286407 | 10/2002 |
| JP | 2002-543421 | 12/2002 |
| JP | 2003-098036 | 4/2003 |
| JP | 2003-168114 | 6/2003 |
| JP | 2003-266003 | 9/2003 |
| JP | 2004-086539 | 3/2004 |
| JP | 2004-279282 A | 10/2004 |
| JP | 2004-279367 A | 10/2004 |
| JP | 2005-077181 | 3/2005 |
| JP | 2005-202268 | 7/2005 |
| JP | 2005-249633 | 9/2005 |
| JP | 2006-067423 A | 3/2006 |
| JP | 2006-145484 | 6/2006 |
| JP | 2006-171453 | 6/2006 |
| JP | 2006-184125 | 7/2006 |
| JP | 2006-319598 A | 11/2006 |
| JP | 2007-024873 | 2/2007 |
| JP | 200734648 A | 2/2007 |
| JP | 2007-171029 A | 7/2007 |
| JP | 2007-172512 A | 7/2007 |
| JP | 2007-184872 A | 7/2007 |
| JP | 2007-199037 | 8/2007 |
| JP | 2008-020431 | 1/2008 |
| JP | 2008-139027 | 6/2008 |
| JP | 2008-164303 | 7/2008 |
| JP | 2008-242191 | 10/2008 |

\* cited by examiner

COLOR FILTER INSPECTION METHOD, COLOR FILTER MANUFACTURING METHOD, AND COLOR FILTER INSPECTION APPARATUS

TECHNICAL FIELD

The present invention relates to methods for inspecting, for unevenness, color filters of liquid crystal displays for use in color televisions, personal computers, and the like, methods for manufacturing color filters with little unevenness, and apparatuses for inspecting color filters for unevenness. In particular, the present invention relates to a color filter inspection method and the like for early detecting, through macroscopic observation of a color filter, unevenness that occurs in a color filter manufacturing step such as a drying step.

BACKGROUND ART

In recent years, liquid crystal display devices have been made larger, and there has been a tendency toward a growing demand for large liquid crystal display devices. However, cost reduction is required for further widespread use. Accordingly, there has been a growing demand for cost reduction in color filters, for color filters are high in cost ratio. In particular, it is important to raise yields, for yields directly affect costs. Accordingly, there has been a growing demand for the accurate detection of defects in color filters.

Conventional examples of methods for manufacturing color filters include a staining method, a pigment dispersion method, an electrodeposition method, and a printing method. However, each of these methods requires repetition of the same step for putting colors red, blue, and green. The large number of steps causes a decrease in yield and an increase in cost of liquid crystal displays.

Proposed in view of this is an ink-jet method for forming a color filter by discharging a color filter member onto a transparent substrate with use of an ink-jet head. The ink-jet method makes it possible to form red, blue, and green in one step, and therefore makes it possible to bring about a drastic cost-reducing effect such as simplification of manufacturing steps.

However, since the ink-jet method uses the ink-jet head, the color filter member is in liquid form. This makes it necessary to dry the color filter member discharged onto the transparent substrate. In the step of drying the color filter, the color filter starts to dry at the periphery thereof. This makes it difficult for the color filter to be uniform in shape across the substrate, thus causing a change in shape mainly near a boundary between the color filter and a black matrix. It is this change that causes slight unevenness of luminance.

Proposed in view of this is an inspection method for extracting a defect by conducting various inspections at the time of production of a color filter after a drying step, an example of which method is a technique, relating to detection of a defect such as a minute foreign body on a color filter, which detects a foreign body by illuminating a color filter from directions different between an outward movement of the color filter and a homeward movement of the color filter, by imaging diffuse reflected light, by converting a pattern of steps in the outward movement and the homeward movement into binary data, and by taking cognizance through a logic operation AND (Patent Document 1).

Patent Document 1: Japanese Unexamined Patent Application Publication No. 20065/1995 (Tokukaihei 7-20065; published on Jan. 24, 1995)

DISCLOSURE OF THE INVENTION

However, the image, obtained by imaging the diffuse reflected light, which is used by the conventional method of Patent Document 1 has no grayscale produced therein. This undesirably makes it impossible to detect a cause of unevenness of luminance, i.e., a change in shape near a boundary between the color filter and a black matrix. That is, in the case of the image obtained by imaging the diffuse reflected light, e.g., in the case of the image obtained by macroscopically imaging the whole substrate, the imaging system is struck by light reflected by a part other than the edge of the color filter member (especially by a central part). The light reflected by the central part is more intense and less in luminance difference than that reflected by the edge, and therefore cancels out a difference in luminance on the edge of the color filter member. Therefore, the image has no grayscale produced therein.

Further, even if the color filter member is imaged microscopically, the light reflected by the central part is more intense than that reflected by the edge. Accordingly, even when the amount of light is increased to such a level that the difference in luminance of the light reflected by the edge can be detected or even when imaging sensitivity is increased, the imaging system is saturated in consequence of the light reflected by the central part. Therefore, the image has no grayscale produced therein.

The present invention has been made in view of the foregoing problems. It is an object of the present invention to provide a color filter inspection method for early detecting unevenness that occurs in a color filter manufacturing step such as a drying step, a color filter inspection apparatus, and a color filter manufacturing method that involves the use of the color filter inspection method.

In order to solve the foregoing problems, a color filter inspection method according to the present invention is a method for inspecting, for unevenness, a color filter in which each pixel is surrounded by a black matrix, the method including: an illuminating step of illuminating a color filter edge at an angle of incidence inclined at not less than 0 degree to less than (90+α) degrees to a line normal to that principal surface of a substrate on which the color filter has been formed or at an angle of incidence inclined at not less than 0 degree to less than (90−α) degrees to the line normal to the principal surface of the substrate, the color filer edge containing a boundary between the pixel and the black matrix, a being an average degree of inclination of the color filter edge that is not less than 0 degree to less than 90 degrees; an imaging step of taking at least two images of light reflected by the color filter edge at an angle of reflection, different from the angle of incidence, which is not less than 0 degree to less than (90−α) degrees when the angle of incidence is not less than 0 degree to less than (90+α) degrees or is not less than 0 degree to less than (90+α) degrees when the angle of incidence is not less than 0 degree to less than (90−α) degrees; a shot-image information analyzing step of calculating a difference in luminance within the color filter in accordance with the images thus taken; and an unevenness determining step of determining the existence of unevenness of the color filter from the difference in luminance.

According to the foregoing method, the color filter edge, containing a boundary between the pixel and the black matrix, where unevenness is likely to occur in a drying step or the like is illuminated at an appropriate angle, and light reflected at an angle different from an angle of specular reflection of light is imaged. Therefore, as with the technique of Patent Document 1, which uses diffuse reflected light, the imaging system is hardly struck by light reflected by a part other than the color filter edge. This makes it easy to make a difference in luminance within an image taken by the imaging system.

This makes it possible to highly accurately detect unevenness occurring from a minute change in surface shape that is caused by a color filter manufacturing step such as a drying step. Further, since at least two images of diffuse reflected light are taken and the existence of unevenness is determined from a difference in luminance within the color filter in accordance with the images thus taken, the color filter can be macroscopically inspected for unevenness over a wider range.

In the color filter inspection method, the illuminating step may be a step of illuminating two or more difference color filter edges per pixel from different illuminating directions at least one of which is opposite another with respect to a surface including the line normal to that principal surface of the substrate on which the color filter has been formed.

Color filter edges vary in surface slope depending on a drying step or the like, and are therefore likely to vary in shape. However, since the foregoing method illuminates two or more different color filter edges per pixel from different illuminating directions, the foregoing method makes it possible to obtain images that better reflect variations in shape among the color filter edges. This makes it possible to improve the accuracy of unevenness detection.

Further, the method may be such that the imaging step is a step of imaging light reflected by the two or more different color filter edges per pixel in different imaging directions at least one of which is opposite another with respect to a surface including the line normal to that principal surface of the substrate on which the color filter has been formed.

The foregoing method makes it possible to efficiently trap light, reflected in different directions, by which the color filter edges have been illuminated. This makes it possible to further improve the accuracy of unevenness detection.

In the color filter inspection method, it is preferable that the angle of incidence and the angle of reflection be inclined at more than 0 degree. According to the foregoing method, since the angle of incidence and the angle of reflection are not in a direction normal to that principal surface of the substrate on which the color filter has been formed, the imaging system is not struck by specular reflected light. This makes it easy to make a difference in luminance within an image taken by the imaging system. This makes it possible to improve the accuracy of unevenness detection.

In the color filter inspection method, it is preferable that the angle of incidence and the angle of reflection be at equal angles to a line normal to a tangent passing through a point of inflection of the color filter edge. An inappropriate angle of illumination causes light reflected by a pixel central part of the color filter to be too intense, and therefore makes it impossible to efficiently detect light reflected by the color filter edge. The foregoing method illuminates the color filter at such an appropriate angle that the imaging means is not struck by the light reflected by the pixel central part of the color filter, and therefore makes it possible to efficiently detect the light reflected by the color filter edge. This makes it possible to improve the accuracy of unevenness detection.

Furthermore, in the color filter inspection method, it is preferable that at least two of the imaging directions be perpendicular to two opposing sides of the black matrix.

The black matrix has four sides. According to the foregoing method, since at least two of the imaging directions are perpendicular to two opposing sides of the black matrix, reflected light is imaged from at least two directions of the four sides of the black matrix. Therefore, at least two images different in difference in luminance can be obtained. This enables highly accurate inspection for unevenness.

In the color filter inspection method, the imaging directions may be four directions perpendicular to four sides of the black matrix when the substrate on which the color filter has been formed is observed from a direction normal to the principal surface of the substrate.

Since the foregoing method images reflected light from four directions of the four sides of the black matrix, the foregoing method can macroscopically inspect the color filter for unevenness from all directions of the black matrix. This makes it possible to more highly accurate inspection for unevenness.

In the color filter inspection method, it is preferable that the illuminating step and the imaging step be performed with use of a pair of illuminating means and a pair of imaging means, respectively, the illuminating means and the imaging means being disposed at equal angles to the line normal to the tangent passing through the point of inflection of the color filter edge.

According to the foregoing method, since the two pairs of illuminating means and imaging means are disposed so as to face each other, illumination of color filter edges facing each other and imaging of reflected light can be performed by scanning the substrate once. This makes it possible to shorten inspection takt time.

A color filter inspection apparatus according to the present invention is an apparatus for inspecting, for unevenness, a color filter in which each pixel is surrounded by a black matrix, the apparatus including: illuminating means for illuminating a color filter edge at an angle of incidence inclined at not less than 0 degree to less than ($90+\alpha$) degrees to a line normal to that principal surface of a substrate on which the color filter has been formed or at an angle of incidence inclined at not less than 0 degree to less than ($90-\alpha$) degrees to the line normal to the principal surface of the substrate, the color filer edge containing a boundary between the pixel and the black matrix, a being an average degree of inclination of the color filter edge that is not less than 0 degree to less than 90 degrees; imaging means for taking at least two images of light reflected by the color filter edge at an angle of reflection, different from the angle of incidence, which is not less than 0 degree to less than ($90-\alpha$) degrees when the angle of incidence is not less than 0 degree to less than ($90+\alpha$) degrees or is not less than 0 degree to less than ($90+\alpha$) degrees when the angle of incidence is not less than 0 degree to less than ($90-\alpha$) degrees; shot-image information analyzing means for calculating a difference in luminance within the color filter in accordance with the images thus taken; and unevenness determining means for determining the existence of unevenness of the color filter from the difference in luminance.

According to the foregoing apparatus, the color filter edge, containing a boundary between the pixel and the black matrix, where unevenness is likely to occur in a drying step or the like is illuminated at an appropriate angle, and light reflected at an angle different from an angle of specular reflection of light is imaged. Therefore, as with the technique of Patent Document 1, which uses diffuse reflected light, the imaging system is hardly struck by light reflected by a part other than the color filter edge. This makes it easy to make a difference in luminance within an image taken by the imaging system.

This makes it possible to highly accurately detect unevenness occurring from a minute change in surface shape that is caused by a color filter manufacturing step such as a drying step. Further, since at least two images of diffuse reflected light are taken and the existence of unevenness is determined from a difference in luminance within the color filter in accordance with the images thus taken, the color filter edge can be macroscopically inspected for unevenness over a wider range.

A method according to the present invention for manufacturing a color filter is characterized by supplying, to an inspection step and a step subsequent thereto, only a color filter judged as a conforming product by the color filter inspection method according to the present invention. The foregoing method detects the occurrence of unevenness at any stage in a color filter manufacturing step (such as a drying step) and supplies only a conforming product to the inspection step and the step subsequent thereto, thereby preventing an uneven color filter from passing through the inspection step or the step subsequent thereto. This enables a reduction in manufacturing cost.

Further, a method according to the present invention for manufacturing a color filter is characterized by, when there occurs a color filter judged as a defective product by the color filter inspection method according to the present invention, notifying a color filter manufacturing apparatus of information on the occurrence of the defective product.

The foregoing method detects the occurrence of unevenness at any stage in a color filter manufacturing step (such as a drying step) and feeds back the information to the color filter manufacturing apparatus, thereby preventing a defective product from entering the inspection step or the step subsequent thereto. This enables improvement in yield of liquid crystal displays, thus enabling a reduction in manufacturing cost.

Additional objects, features, and strengths of the present invention will be made clear by the description below. Further, the advantages of the present invention will be evident from the following explanation in reference to the drawings.

Figure 13:
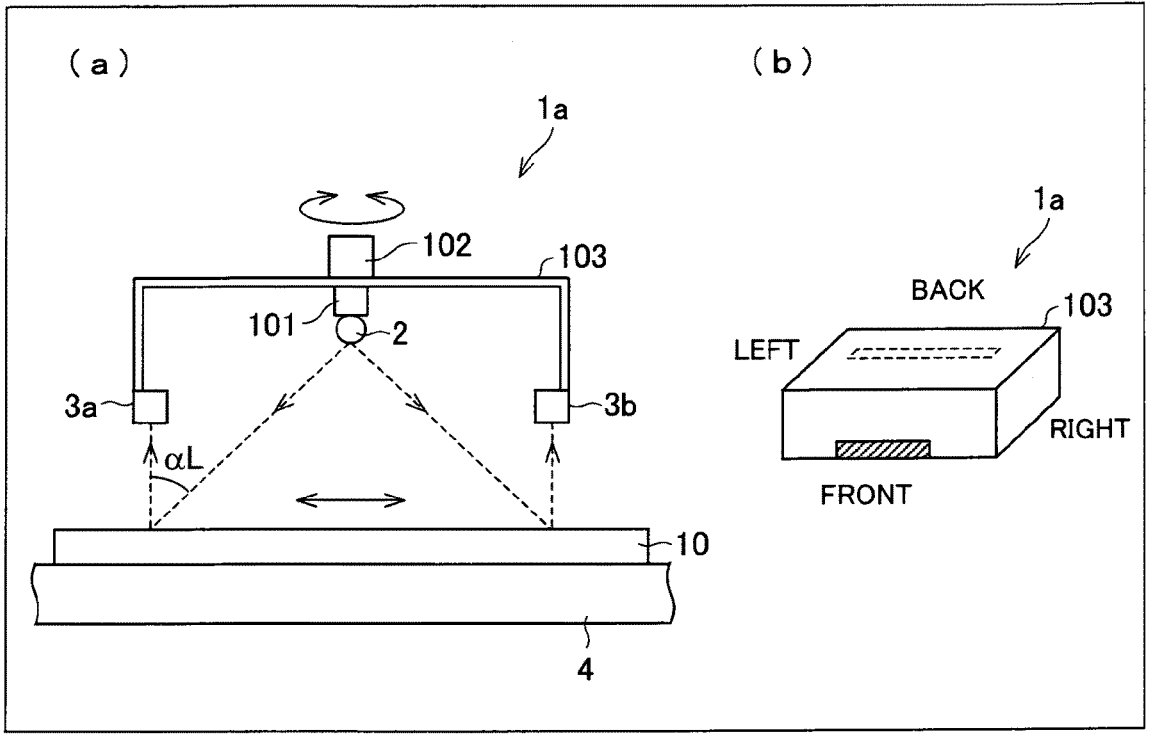

(a) of FIG. 13 is a pattern diagram showing a longitudinal section of an optical system of a color filter inspection apparatus 1a.

(b) of FIG. 13 is a perspective view of the color filter inspection apparatus 1a.

Figure 14:
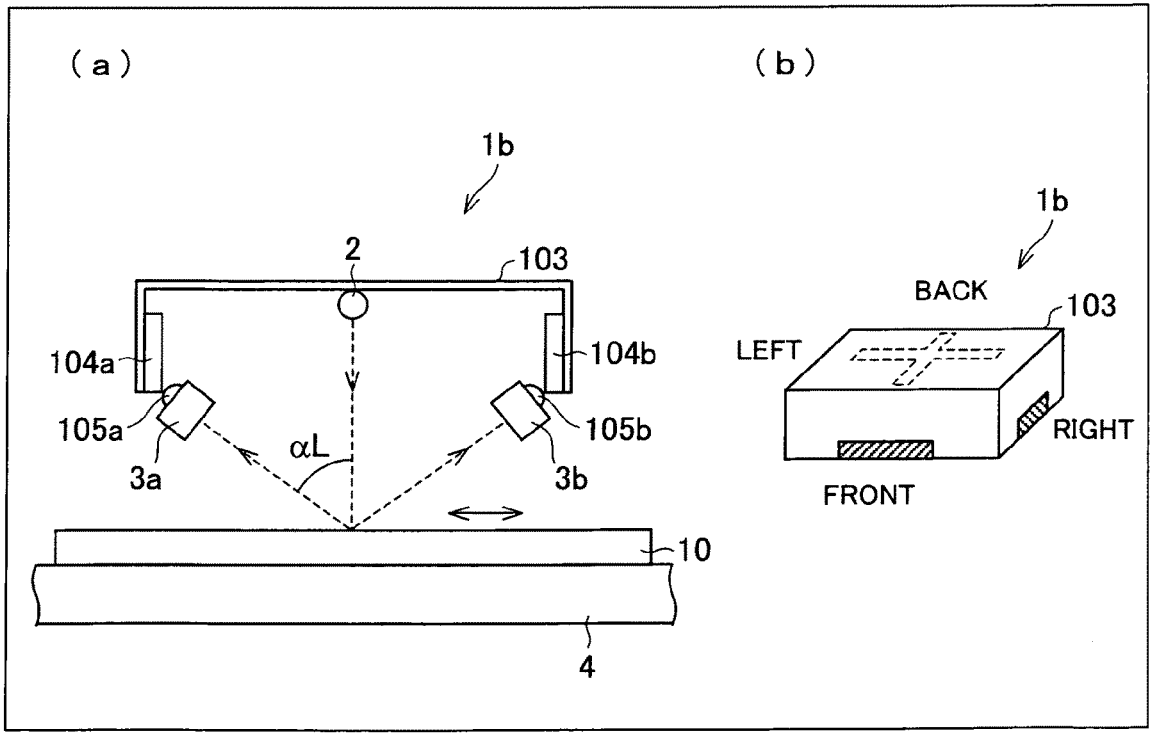

(a) of FIG. 14 is a pattern diagram showing a longitudinal section of an optical system of a color filter inspection apparatus 1b.

(b) of FIG. 14 is a perspective view of the color filter inspection apparatus 1b.

Figure 15:
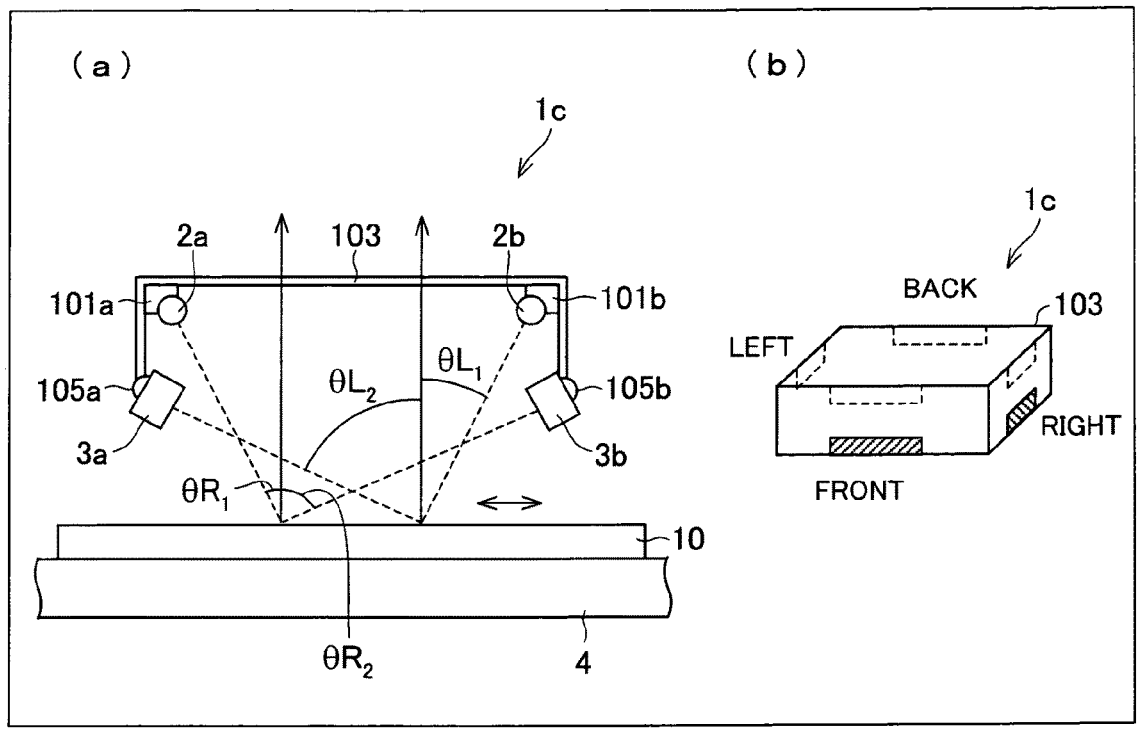

(a) of FIG. 15 is a pattern diagram showing a longitudinal section of an optical system of a color filter inspection apparatus 1c.

(b) of FIG. 15 is a perspective view of the color filter inspection apparatus 1c.

Figure 16:
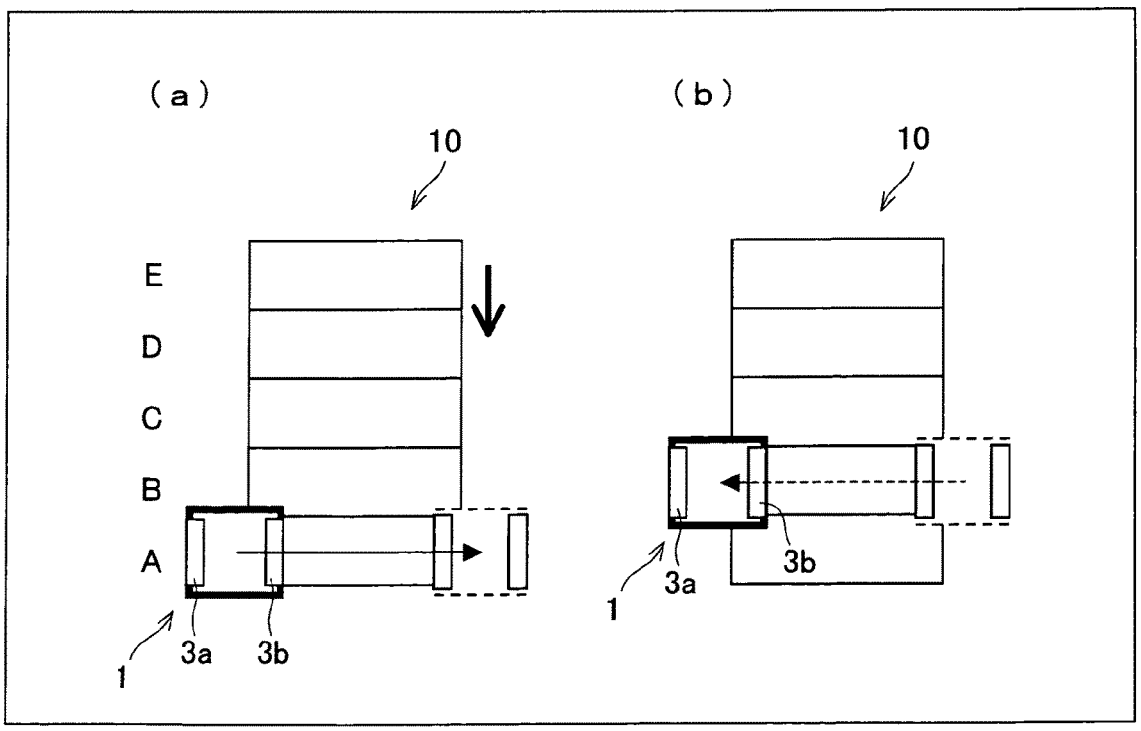

FIG. 16 is a pattern diagram showing the way the color filter 10 is observed, from a direction normal to the principal surface of the substrate, being imaged in directions from side to side, (a) showing the way the Ath row is imaged, (b) showing the way Row the Bth row is imaged.

Figure 17:
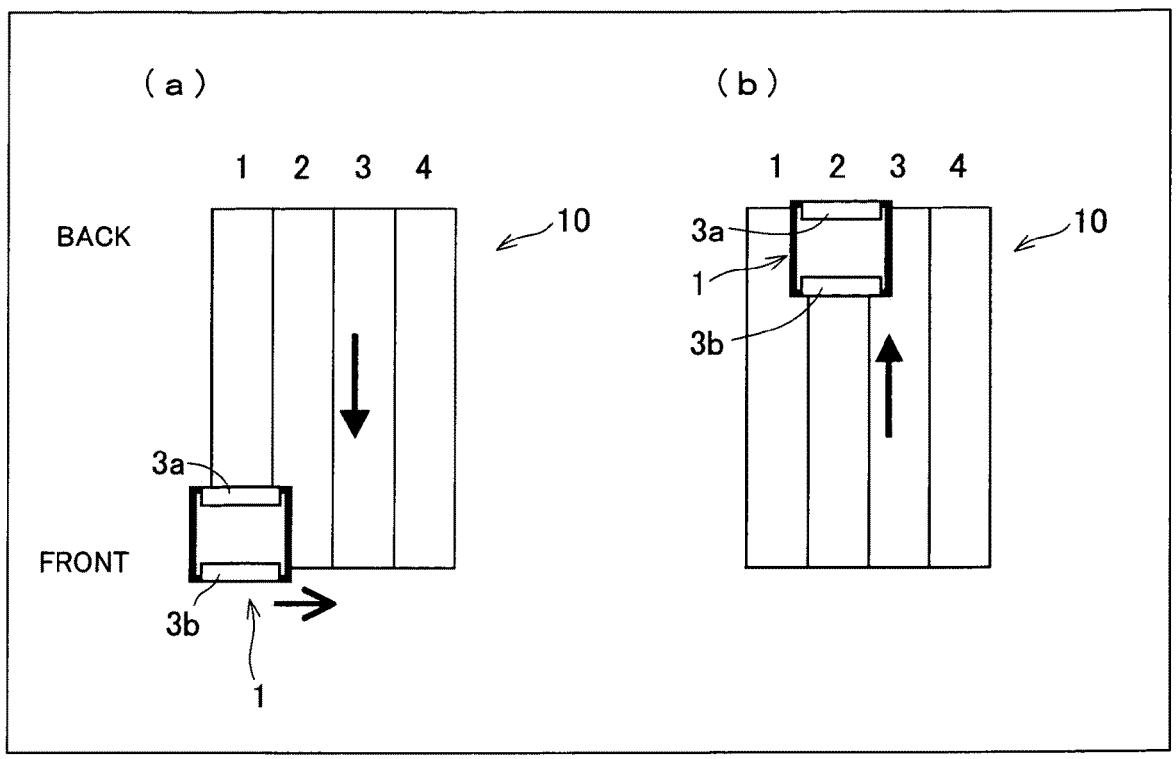

FIG. 17 is a pattern diagram showing the way the color filter 10 is observed, from a direction normal to the principal surface of the substrate, being imaged in anteroposterior directions, (a) showing the way the first column is imaged, (b) showing the way the second column is imaged.

Figure 18:
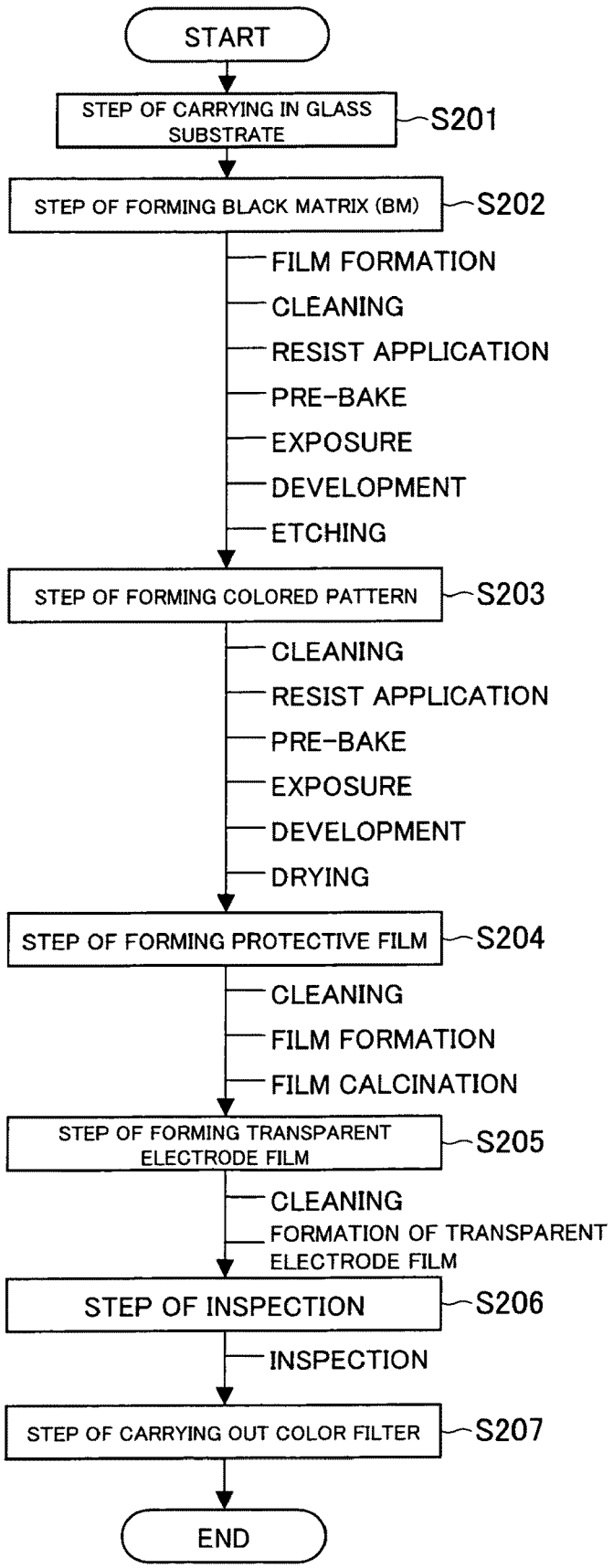

FIG. 18 is a flow chart showing, as a typical example of a color filter manufacturing step, a manufacturing step based on a pigment dispersion method.

REFERENCE NUMERALS

1 Color filter inspection apparatus
1a Color filter inspection apparatus
1b Color filter inspection apparatus
1c Color filter inspection apparatus
2 Illumination lamp (illuminating means)
2a First illumination lamp
2b Second illumination lamp
3 Sensor (imaging means)
3a First sensor
3b Second sensor
6 Control device
7 Storage section
9 Image processing section (shot-image information analyzing means)
10 Color filter
13 Defect determination section (unevenness determining means)
20 Black matrix
21 Pixel
23 Color filter edge
23a Color filter edge
23b Color filter edge
23c Color filter edge 23d Color filter edge
100 Substrate
S3 Illuminating step
S4 Imaging step
S6 Shot-image information analyzing step
S7 Illuminating step
S9 Shot-image information analyzing step
S10 Unevenness determining step

BEST MODE FOR CARRYING OUT THE INVENTION

A color filter inspection method, a color filter inspection apparatus, a color filter manufacturing method each according to the present invention will be described below in various embodiments with reference to FIGS. 1 through 17.

Figure 1:
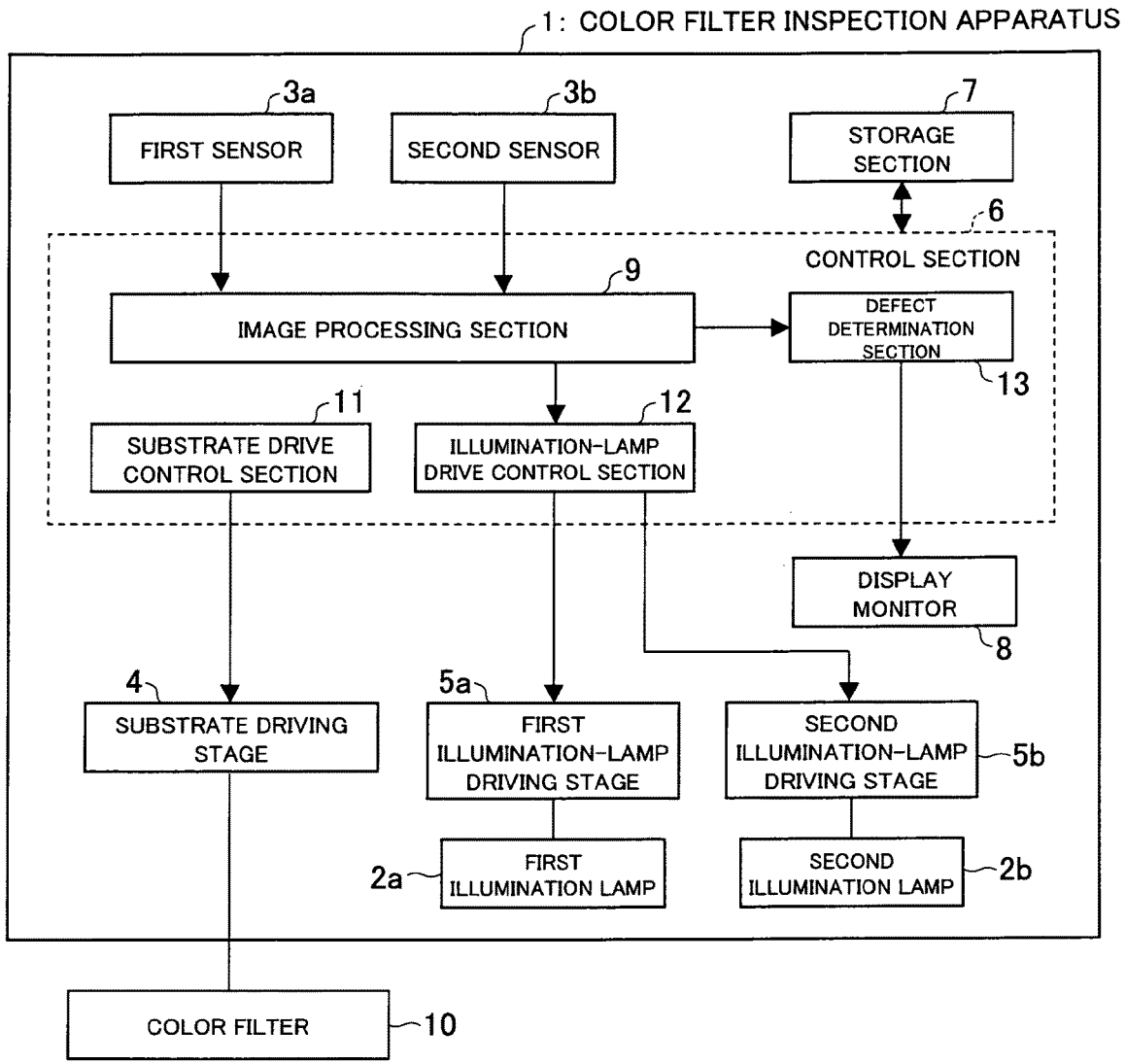
FIG. 1 is a block diagram showing an arrangement of a color filter inspection apparatus 1 according to an embodiment of the present invention.

FIG. 1 is a block diagram showing an arrangement of a color filter inspection apparatus 1 according to the present embodiment. As shown in FIG. 1, the color filter inspection apparatus 1 includes an illumination lamp (illuminating means) 2, a sensor (imaging means) 3, a substrate driving stage 4, an illumination-lamp driving stage 5, a control device 6, a storage section 7, and a display monitor 8. The control section 6 includes an image processing section (shot-image information analyzing means) 9, a substrate drive control section 11, and an illumination-lamp drive control section 12, and a defect determination section (unevenness determining means) 13. The substrate driving stage 4 has a color filter 10 mounted thereon.

Figure 2:
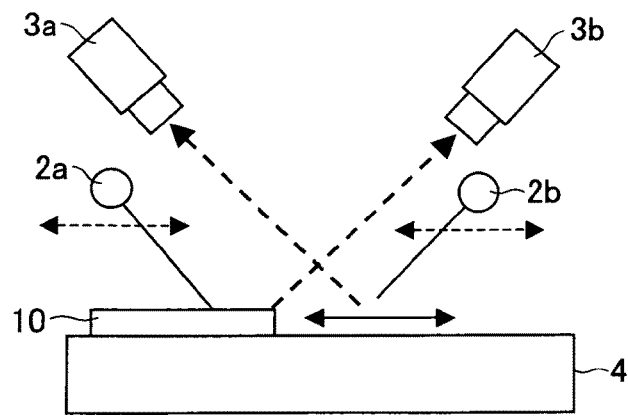
FIG. 2 is a pattern diagram showing an example of an optical system of the color filter inspection apparatus 1 shown in FIG. 1.

Further, FIG. 2 is a pattern diagram showing an example of an optical system of the color filter inspection apparatus 1 shown in FIG. 1.

Figure 3:
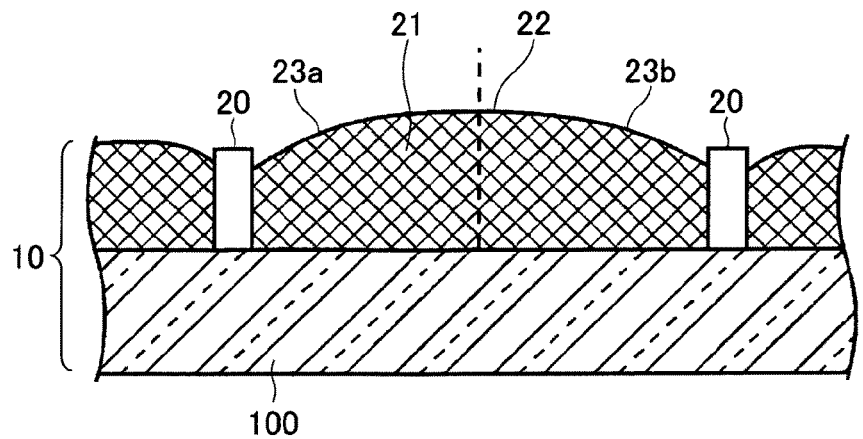
FIG. 3 is a longitudinal sectional view of a color filter 10 made of a liquid color filter member.

FIG. 3 is a longitudinal sectional view of a color filter 10 made of a liquid color filter member. In FIG. 3, the color filter 10 is constituted by a black matrix 20, pixels 21, and a substrate 100. The substrate 100 is made of glass, plastic, or the like. The substrate 100 has the color filter member (black matrix 20, pixels 21) formed thereon. Thus constituted is the color filter 10.

In each present embodiment, examples of the color filter 10, which is to be inspected, include a rectangular plate color filter in which pixels (R, G, B) are arrayed for each color in a substrate-scanning direction, in which the pixels of one color are arrayed in sequence so to be adjacent to the pixels of another color in a direction orthogonal to the substrate-scanning direction, and in which the pixels of each color are surrounded by the black matrix.

The illumination lamp (illuminating means) 2 serves to illuminate the color filter 10. Usable examples of the illumination lamp (illuminating means) 2 include, but are not particularly limited to, a line lamp, an all-round diffuse light (e.g., a striplight), and a beam light.

The line lamp can illuminate the color filter 10 over a certain range, and can therefore illuminate a color filter edge 23 at a predetermined angle over a wide range at a time, thus contributing to a reduction in inspection time. Therefore, the line lamp can be suitably used in particular for the present invention, which macroscopically inspects the whole color filter 10 for unevenness.

The all-round diffuse light can illuminate a 360-degree field. Therefore, the installation of a single all-round diffuse light arranged so that its distance from the color filter 10 can be adjusted makes it possible to illuminate each color filter edge 23 at a predetermined angle, thus contributing to a reduction in size of the apparatus.

The beam light can only illuminate a narrow range at a time, but can illuminate the whole color filter 10 by scanning the color filter 10 or moving the beam light itself over the color filter 10 while illuminating the color filter 10 at a predetermined angle.

The sensor (imaging means) 3 serves to obtain reflected light that is a reflection of illuminating light from the illumination lamp (illuminating means) 2 by a surface of the color filter 10. Examples of the sensor (imaging means) 3 include, but are not limited to, a line sensor and an area sensor. However, in order to macroscopically observe the whole color filter, it is preferable that the color filter 10 illuminated by the illumination lamp (illuminating means) 2 be imaged in the form of a line. Therefore, it is preferable that the line sensor be used.

As shown in FIGS. 1 and 2, the illumination lamp (illuminating means) 2 may be constituted by a first illumination lamp 2a and a second illumination lamp 2b. However, the color filter inspection apparatus 1 is not limited to this, and only needs to include at least one illumination lamp. Similarly, the sensor (imaging means) 3 may be constituted by a first sensor 3a and a second sensor 3b. However, the color filter inspection apparatus 1 is not limited to this, and only needs to include at least one sensor.

The substrate driving stage 4 supports the color filter 10, which is to be inspected, and moves it in directions along a surface of the substrate (in the directions of an arrow indicated by a solid line in FIG. 2; such directions being hereinafter referred to as "substrate-scanning directions"). Further, the substrate driving stage 4 is provided with a mechanism capable of rotating the color filter 10 by 90 degrees.

Examples of methods for rotating the color filter 10 by 90 degrees include: a method for rotating the whole substrate driving stage 4 with use of a rotation mechanism of the substrate driving stage 4 having the color filter 10 mounted thereon; and a method for rotating only the color filter 10 by floating the color filter 10 through discharge of air from a surface of the stage to the color filter 10 and then gripping only a central part of the substrate by suction.

The illumination-lamp driving stage 5 moves the illumination lamp (illuminating means) 2 in a substrate-scanning direction to an appropriate position. In FIG. 1, the illumination-lamp driving stage 5 includes a first illumination-lamp driving stage 5a for the illumination lamp (illuminating means) 2a and a second illumination-lamp driving stage 5b for the illumination lamp (illuminating means) 2b. However, the present invention is not limited to this. For example, a single illumination-lamp driving stage may drive a plurality of illumination lamps (illuminating means) 2.

The storage section 7 is a section on which to save data on each position of the illumination-lamp driving stage 5 as model information. The data is obtained through experimental measurement of perfect positional data on the illumination-lamp driving stage 5 for obtaining a direction from which each image is taken. The experimental measurement is performed with use of an even reference sample identical in model (arranged identically in pixel size, color filter member, quantity, and the like) to the color filter 10, which is to be inspected.

The display monitor 8 displays a result of a determination (defect information) made by the defect determination section 13 and causes an apparatus administrator (operator) to recognize the result.

The image processing section 9 accumulates information on images taken by the sensor 3, creates a two-dimensional image of the surface of the color filter 10, and analyzes the image thus created.

In accordance with model information sent from the storage section 7 about the color filter 10, the substrate drive control section 11 uses the substrate driving stage 4 to cause the color filter 10 to be scanned with constant speed.

In accordance with that positional data information on the illumination-lamp driving stage 5 which corresponds to the model information sent from the storage section 7 about the color filter 10, the illumination-lamp drive control section 12 uses the illumination-lamp driving stage 5 to move the illumination lamp (illuminating means) 2.

The defect determination section 13 determines the state of unevenness of the color filter 10 in accordance with data obtained by analyzing the shot image of the surface of the color filter 10.

The color filter inspection method according to the present invention causes an illumination lamp (illuminating means) 2 to illuminate a color filter edge 23 at an angle of incidence inclined at not less than 0 degree to less than (90+α) degrees to a line normal to a principal surface of the substrate 100 or at an angle of incidence inclined at not less than 0 degree to less than (90−α) degrees to the line normal to the principal surface of the substrate 100, the color filter edge 23 containing a boundary between the pixel 21 and the black matrix 20, a being an average angle of inclination of the color filter edge 23 that is not less than 0 degree to less than 90 degrees.

The term "color filter edge" in the present specification means a region that contains a boundary between the whole length of one side of the black matrix and the pixel. Normally, a single pixel of a color filter takes the shape of a quadrangle surrounded by four sides of a black matrix. Therefore, with attention focused on one side, the four sides have their respective color filter edges.

Since the color filter edge is a region that contains a boundary between the whole length of one side of the black matrix and the pixel, and therefore does not contain the whole length of another side opposite the one side of the black matrix. The region corresponding to the color filter edge can vary depending on the material of the color filter, the material of the black matrix, a method for water-shedding or water-attracting treatment, and the like. However, for example, in the case of a pixel with the dimension 400 μm×400 μm, there is a change in shape of a region falling with a distance of 20 μm (approximately 5%) from a place of contact with the black matrix. Therefore, the region serves as a color filter edge.

Further, the color filter edge may contain only the boundary. The color filter edge may vary in inclination depending on a drying step or the like, and is therefore a part prone to unevenness. Therefore, it is possible to detect unevenness with high accuracy by illuminating the color filter edge at the after-mentioned angle and then imaging reflected light. In particular, the boundary between the black matrix and the pixel is a part particularly prone to unevenness. Therefore, it is possible to detect unevenness with higher accuracy by illuminating the boundary. However, it is not necessary to illuminate only the boundary, and it is only necessary to illuminate a region that contains the boundary.

The principal surface of the substrate 100 means a surface having the color filter formed thereon. In FIG. 3, the principal surface of the substrate 100 is a surface of boundary between the color filter 10 and the substrate 100. The angle inclined from the line normal to the principal surface of the substrate 100 means how many degrees the angle of incidence is inclined at to the line normal to the principal surface of the substrate 100. In cases where the angle inclined from the line normal to the principal surface of the substrate 100 is 0 degree, light strikes the color filter edge 23 from a direction perpendicular to the principal surface.

The average angle of inclination of the color filter edge means an average angle at which the color filter edge slopes away from the substrate.

As shown in FIG. 3, the color filter edge often has a surface that slopes so as not to be parallel to the substrate, may vary in inclination depending on the drying step or the like, and is therefore prone to unevenness. The angle of inclination varies with location in the color filter. Therefore, the present specification defines the average angle of inclination of the color filter edge as the average of angles that tangents drawn from a point of intersection of the black matrix, the substrate, and the color filter edge to the color filter edge form with the substrate.

The angle at which the color filter edge slopes away from the substrate can be predicted depending on the size of the pixel, the members of the color filter, and a method for water-shedding or water-attracting treatment, and can be calculated by performing measurements in advance by a stylus surface shape measuring instrument with use of a statistical database or the like.

In the following, a tangent drawn from a point of intersection of the black matrix, the substrate, and the color filter edge to the color filter edge will be referred to as "tangent passing through a point of inflection of the color filter edge".

Figure 4:
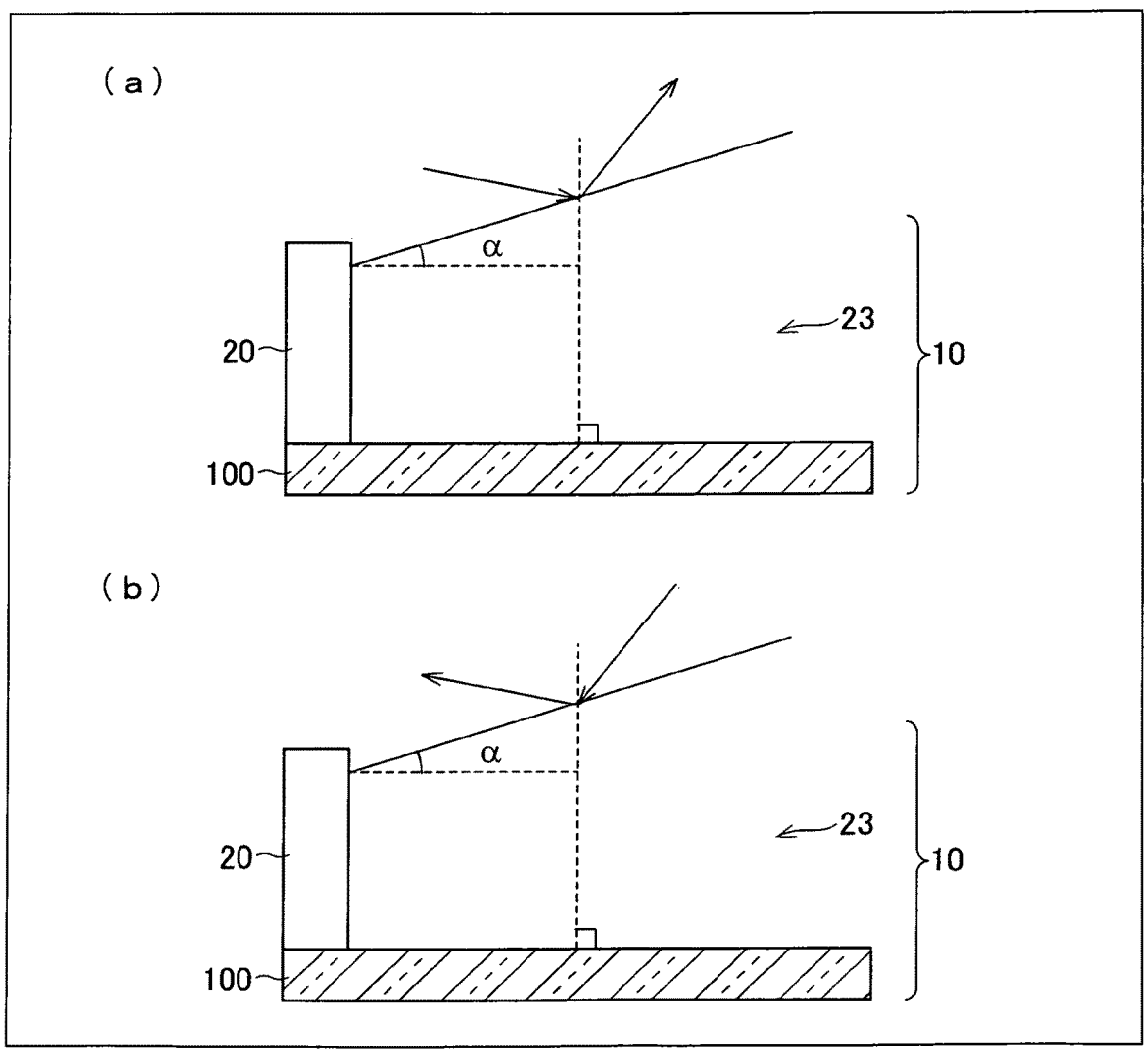
FIG. 4 is an enlarged view of a color filter edge 23 shown in FIG. 3, (a) being a pattern diagram showing the way light is made to shine at an angle of incidence inclined at not less than 0 degree to less than (90+α) degrees to a line normal to a principal surface of the substrate 100, (b) being a pattern diagram showing the way light is made to shine at an angle of incidence inclined at not less than 0 degree to less than (90−α) degrees to the line normal to the principal surface of the substrate.

FIG. 4 is an enlarged view of a color filter edge 23 shown in FIG. 3. (a) of FIG. 4 is a pattern diagram showing the way light is made to shine at an angle of incidence inclined at not less than 0 degree to less than (90+α) degrees to a line normal to a principal surface of the substrate 100. (b) of FIG. 4 is a pattern diagram showing the way light is made to shine at an angle of incidence inclined at not less than 0 degree to less than (90−α) degrees to the line normal to the principal surface of the substrate.

The light made to shine on the color filter edge 23 is reflected by the color filter 23 either at an angle of reflection of not less than 0 degree to less than (90−α) degrees when the angle of incidence is not less than 0 degree to less than (90+α) degrees, or at an angle of reflection of not less than 0 degree to less than (90+α) degrees when the angle of incidence is not less than 0 degree to less than (90−α) degrees. The reflected light is imaged by the sensor (imaging means) 3.

In (a) of FIG. 4, it is only necessary that the angle of incidence be not less than 0 degree to less than (90+α) degrees. However, the illumination lamp (illuminating means) 2 illuminates the color filter edge 23 more easily from the upper side of the substrate 100, it is preferable that the angle of incidence be not less than 0 degree to less than 90 degrees. Further, in (b) of FIG. 4, it is only necessary that the angle of reflection be not less than 0 degree to less than (90+α) degrees. However, since the reflected light is received and imaged more easily on the upper surface of the substrate 100, it is preferable that the angle of reflection be not less than 0 degree to less than 90 degrees.

That is, although not particularly limited, it is preferable that the color filter edge 23 be illuminated at such an angle of incidence that the upper side of the substrate 100 is illuminated, and that the color filter edge 23 reflects light at such an angle of reflection that the light is received and imaged on the upper side of the substrate 100.

Further, when the illumination lamp (illuminating means) 2 does not provide illumination at an appropriate angle, light reflected by a pixel central part 22 is so intense that light reflected by the color filter edge 23 cannot be efficiently detected. In the step of drying the color filter member discharged onto the color filter 10, there is no change in shape of the pixel central part 22, but there is a slight change in shape of the color filter edge 23. It is this change that causes unevenness.

Therefore, when the sensor (imaging means) 3 is struck by the intense reflected light from the pixel central part 22, the light reflected by the color filter edge 23 is negated and becomes hard to observe. In order to efficiently detect the light reflected by the color filter edge 23, it is preferable that the sensor (imaging means) 3 be struck by as little reflected light as possible from the pixel central part 22.

In order to efficiently detect the light reflected by the color filter edge 23, the angle of illumination is adjusted by moving the illumination lamp (illuminating means) 2 in parallel with a substrate-scanning direction of the illumination-lamp driving stage 5.

Figure 5:
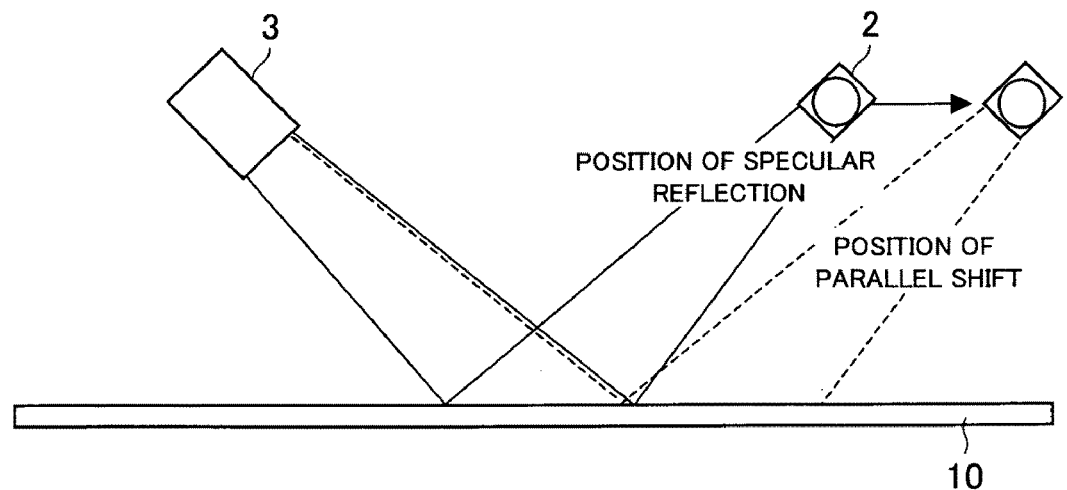
FIG. 5 is a pattern diagram explaining the way an optimum angle of illumination is determined by moving an illumination lamp (illuminating means) 2 in parallel.

FIG. 5 is a pattern diagram explaining the way an optimum angle of illumination is determined by moving the illumination lamp (illuminating means) 2 in parallel.

The angle of illumination depends on the average angle of inclination of the color filter edge 23. Microscopically, in a position of specular reflection (i.e., in such a position that the sensor (imaging means) 3 is struck by the center of illumination from the illumination lamp (illuminating means) 2) of FIG. 5, the illumination from the illumination lamp (illuminating means) 2 enables reflection from the whole surface of the color filter 10. In this case, the sensor (imaging means) 3 is struck by the light reflected by the central portion (pixel central portion 22) of the color filter 10. Since the light reflected by the central portion (pixel central portion 22) of the color filter 10 is intense as described above, the light reflected by the color filter edge 23 becomes hard to observe.

In view of this, by moving the illumination lamp (illuminating means) 2 in parallel from the position of specular reflection as shown in FIG. 5, the sensor (imaging means) 3 is prevented from being struck by the light reflected by the central portion (pixel central portion 22) of the color filter 10. This makes it easier for the sensor (imaging means) 3 to detect the light reflected by the color filter edge 23. As a result, the accuracy of unevenness detection can be improved.

Figure 6:
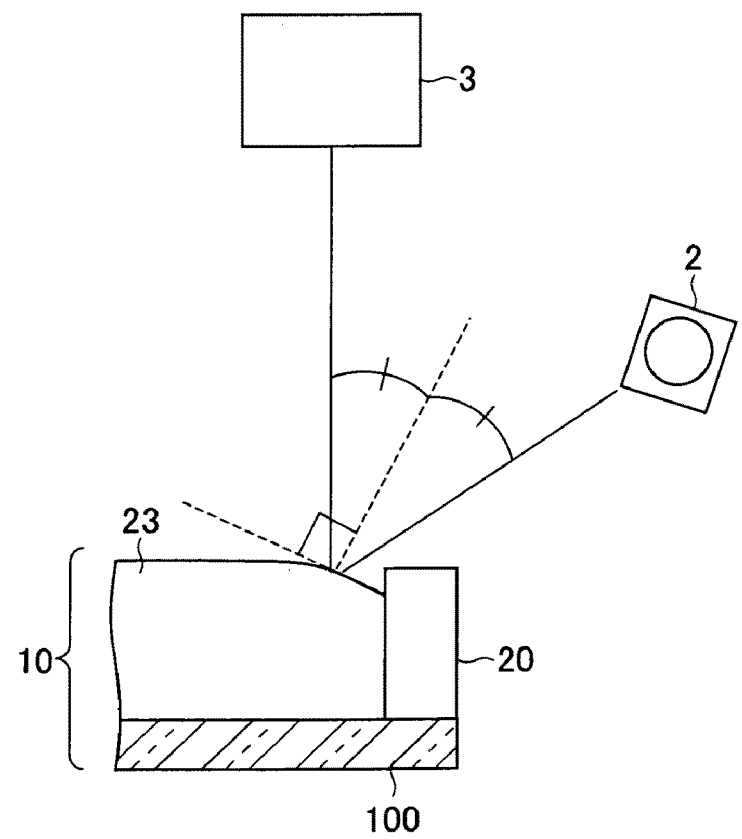
FIG. 6 shows the way the color filter edge 23 is struck by and reflects light in cases where the illumination lamp (illuminating means) 2 is moved in parallel so that light reflected by a central portion (pixel central portion 22) of the color filter 10 is prevented from striking a camera.

FIG. 6 shows the way the color filter edge 23 is struck by and reflects light in cases where the illumination lamp (illuminating means) 2 is moved in parallel so that light reflected by a central portion (pixel central portion 22) of the color filter 10 is prevented from striking a camera. In this case, as shown in FIG. 6, the angle of incidence and the angle of reflection are at equal angles to a line normal to a tangent passing through a point of inflection of the color filter edge 23.

The distance the illumination lamp (illuminating means) 2 and the sensor (imaging means) 3 move in parallel over the illumination-lamp driving stage 5 from the point of specular reflection in a substrate-scanning direction to such a position that the color filter edge 23 is efficiently illuminated can be predicted by a preliminary experiment, provided conditions such as the size of pixels of the color filter, the width of the black matrix, the amount of the color filter member, and the water-attracting or water-shedding effects of the black matrix and the color filter member are identical.

Examples of methods for predicting such positions of the illumination lamp (illuminating means) 2 and the sensor (imaging means) 3 that the color filter edge 23 can be efficiently illuminated include a method for setting an angle of incidence by measuring the angle of the edge 23 of a color filter formed in advance, by imaging light incident at several angles different by ±0.1 degrees from the angle, by using marginally conforming and defective products at each angle to check quantitative numerical values at which unevenness is detected, and by setting as an angle of incidence a quantitative numerical value at which detection sensitivity is at the best.

Experimental calculation of such positions in advance that the color filter edge 23 can be efficiently illuminated and accumulation of the positions in the storage section 7 make it possible to read positional data on the illumination-lamp driving stage 5 from the storage section 7 in inspecting the color filter 10, which is an object model, and to set the position of the illumination lamp (illuminating means) 2 before taking an image with the sensor (imaging means) 3.

As described above, when α is an average angle of inclination of the color filter edge 23 that is not less than degree to less than 90 degrees, the angle of incidence only needs to be inclined at not less than 0 degree to less than (90+α) degrees to the line normal to the principal surface of the substrate 100 or at not less than 0 degree to less than (90−α) degrees to the line normal to the principal surface of the substrate. The angle of reflection only needs to be an angle different from the angle of incidence, i.e., either an angle of reflection of not less than 0 degree to less than (90−α) degrees when the angle of incidence is not less than 0 degree to less than (90+α) degrees, or an angle of reflection of not less than 0 degree to less than (90+α) degrees when the angle of incidence is not less than 0 degree to less than (90−α) degrees. In order to avoid the situation where the light reflected by the pixel central part 22 is so intense that the light reflected by the color filter edge 23 cannot be efficiently detected, it is preferable that the angle of incidence not be inclined at 0 degree.

In other words, it is preferable that the angle of incidence and the angle of reflection be inclined from the line normal to the principal surface of the substrate 100. When the angle of incidence and the angle of reflection are inclined from the line normal to the principal surface of the substrate 100, the sensor (imaging means) 3 is not struck by specular reflected light. This makes it easier to differentiate the color filter edge in luminance from the other part.

Further, in cases where the imaging direction is a direction normal to the principal surface of the substrate 100, i.e., in cases where the angle of reflection is inclined at 0 degree, a housing for the illumination lamp (illuminating means) 2 and a housing for the sensor (imaging means) 3 interferes with each other, because the average angle of inclination of the color filter edge 23 is inherently as small as 2 to 3 degrees. In view of this, it is preferable that the angle of reflection be inclined from the line normal to the principal surface of the substrate 100.

It is more preferable that, as shown in FIG. 6, the angle of incidence and the angle of reflection be at equal angles to a line normal to a tangent passing through a point of inflection of the color filter edge. In this case, the sensor (imaging means) 3 is prevented from being struck by the light reflected by the pixel central part 22 of the color filter 10, so that the light reflected by the color filter edge 23 can be efficiently detected. This makes it possible to improve the accuracy of unevenness detection.

It is necessary that the angle of reflection be an angle different from the angle of incidence. That is, the angle of incidence and the angle of reflection are inclined at different angles to the line normal to the principal surface of the substrate 100. In cases where the angle of incidence and the angle of reflection are identical, i.e., in the case of specular reflection, the sensor (imaging means) 3 is struck by the light reflected by the central portion (pixel central portion 22) of the color filter 10, so that the light reflected by the color filter edge 23 becomes hard to observe.

The sensor (imaging means) 3 takes at least two images of light reflected by the color filter edge 23. The "at least two images" are not particularly limited, but are preferably images of reflections of light made to shine on two or more different color filter edges 23 per pixel 21. The number of pieces of information for making a determination in inspecting the pixels 21 for unevenness is made larger and the possibility of overlooking unevenness occurring in other sites is made lower by imaging reflections of light made to shine on two different color filter edges 23 per pixel 21 than by imaging a reflection of light made to shine on a single color filter edge 23 per pixel 21. This is preferable from the point of view of conducting high-accuracy inspections. From this point of view, it is more preferable to image reflections of light made to shine on three different color filter edges 23 per pixel 21, or particularly preferable to image reflections of light made to shine on four different color filter edges 23 per pixel 21.

Figure 7:
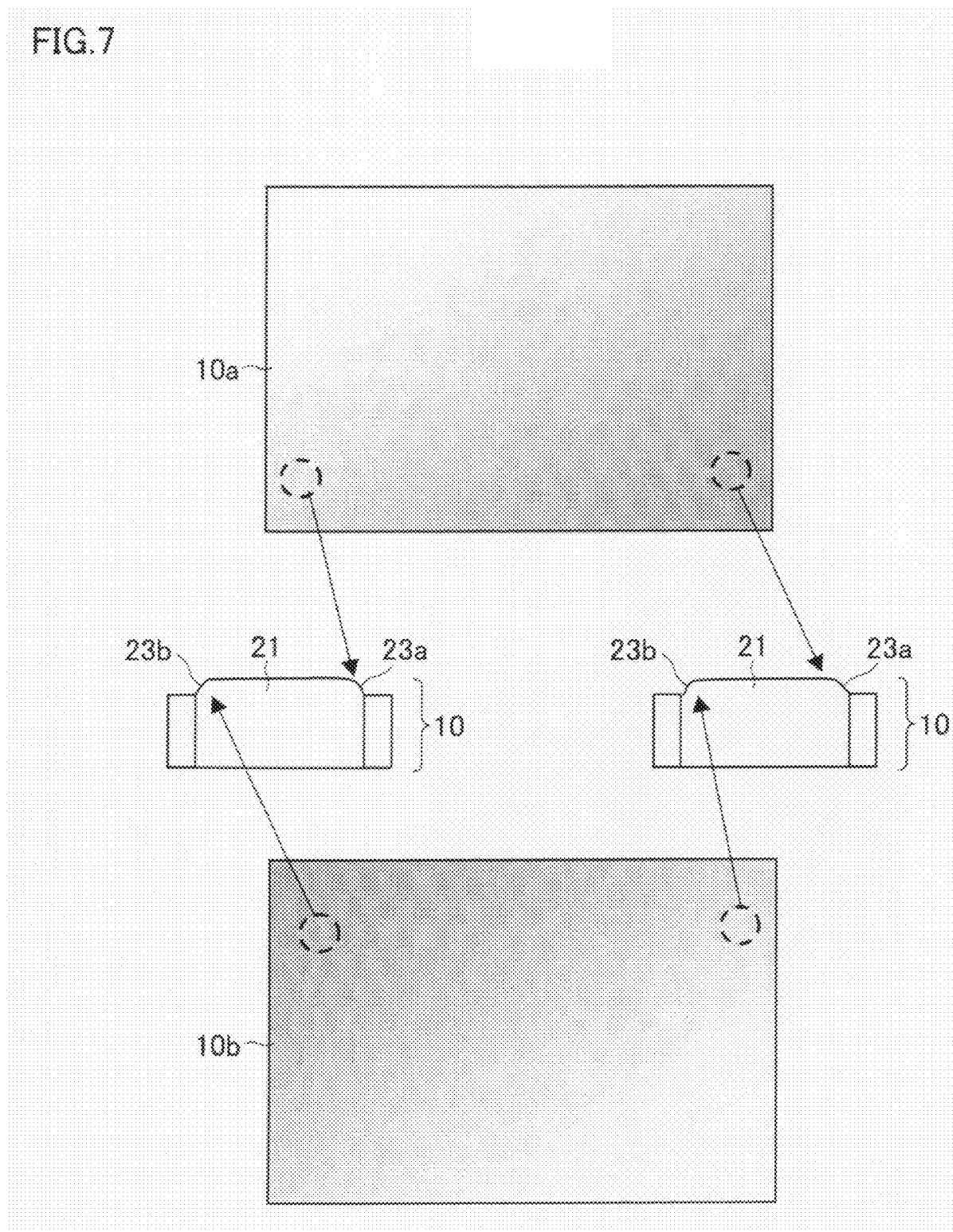
FIG. 7 is a pattern diagram showing that images obtained by imaging two different color filter edges per pixel are different in luminance.

FIG. 7 is a pattern diagram showing that images obtained by imaging two different color filter edges per pixel are different in luminance. In the longitudinal sectional view of a single pixel 21 of the color filter 10 shown in FIG. 7, the color filter edges 23a and 23b differ in shape from each other mainly due to the drying step. Therefore, the shot image (10a) of light made to efficiently shine on the color filter edge 23a and the shot image (10b) of light made to efficiently shine on the color filter edge 23b are different in luminance.

That is, since the shot images of light made to shine on the two different color filter edges 23a and 23b per pixel are different in luminance. This means that two pieces of information for making a determination in unevenness inspection are obtained per pixel. Therefore, the accuracy of inspection is made higher than by inspecting the color filter for unevenness solely in accordance with a shot image of light made to shine on a single color filter edge per pixel.

It is preferable that the color filter 10 be illuminated such that two or more different color filter edges are illuminated per pixel from different illuminating directions at least one of which is opposite another with respect to a surface including the line normal to that principal surface of the substrate on which the color filter has been formed.

Figure 8:
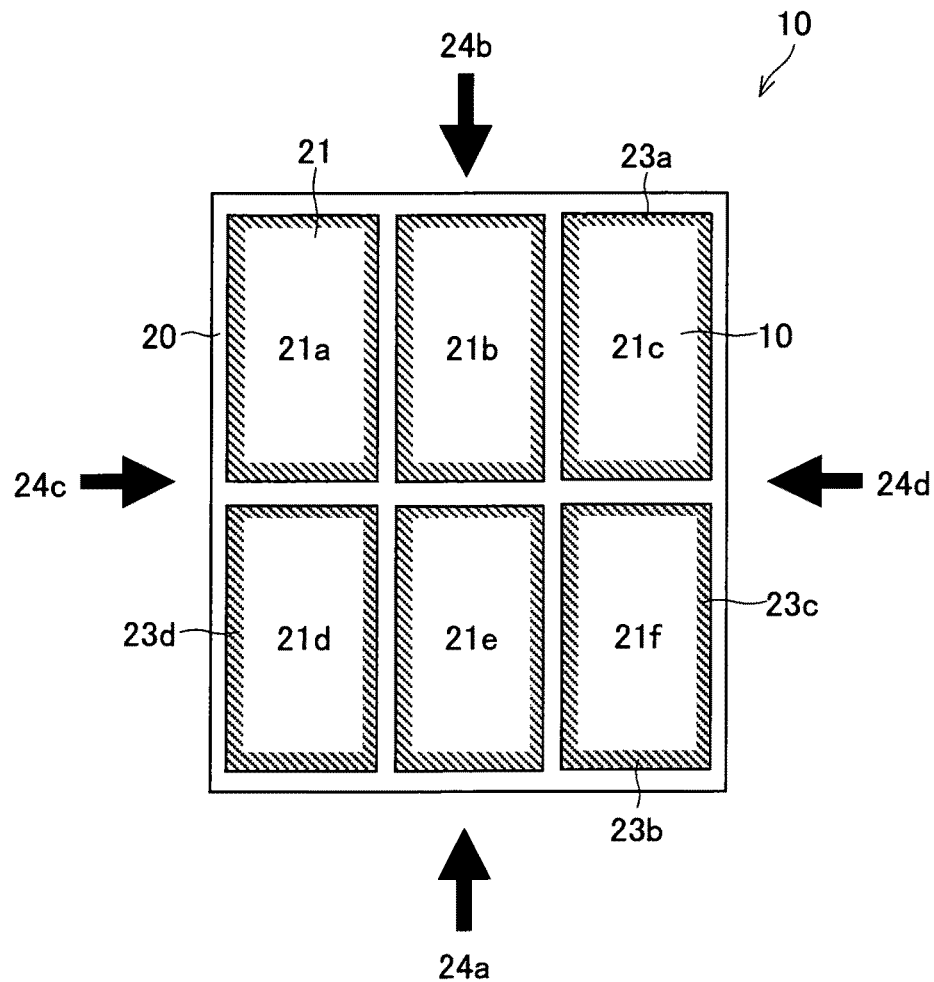
FIG. 8 shows the color filter 10 microscopically.

FIG. 8 shows the color filter 10 microscopically. FIG. 8 shows pixels 21a to 21f each surrounded by the black matrix 20. For example, the pixel 21a forms color filter edges 23a to 23d with the black matrix 20. Further, FIG. 8 shows an aspect in which the color filter edges 23a to 23d of each of the pixels 21a to 21f of the color filter 10 are illuminated from four different illuminating direction 24a to 24d at least one of which is opposite another with respect to a surface including the line normal to that principal surface of the substrate on which the color filter has been formed. For example, the illuminating direction 24a is opposite the illuminating direction 24b with respect to a surface including the line normal to the substrate, and the illuminating direction 24c is opposite the illuminating direction 24d with respect to a surface including the line normal to the substrate.

In FIG. 8, for convenience, the color filter edges 23a to 23d are represented by shaded portions near the borders with the black matrix 20. However, the color filter edges 23a to 23d are not necessarily limited to these.

The shapes of the color filter edges 23a to 23d are affected mainly by the drying step, and therefore are not necessarily identical. The shapes of the color filter edges 23a to 23d cause unevenness of luminance when a liquid crystal panel is manufactured, and the unevenness of luminance may result in a defective product. Therefore, it is necessary to detect unevenness at the time of production of the color filter 10.

In order to for the color filter edge 23a to be inspected, the color filter edge 23a can be illuminated more efficiently when illuminated from the illuminating direction 24a shown in FIG. 8. Although is possible to illuminate the color filter edge 23a from the illuminating direction 24b in order to inspect the color filter edge 23a, it is preferable to illuminate the color filter edge 23a from the illuminating direction 24a. The reason for this is as follows: While the illuminating direction 24a is a direction in which to move the illumination lamp (illuminating means) 2 away from the sensor (imaging means) 3, the illuminating direction 24b is a direction in which to move the illumination lamp (illuminating means) 2 closer to the sensor (imaging means) 3, and is therefore limited in distance.

Similarly, it is preferable to illuminate the color filter edge 23b from the illuminating direction 24b in order to inspect the color filter edge 23b, to illuminate the color filter edge 23c from the illuminating direction 24c in order to inspect the color filter edge 23c, and to illuminate the color filter edge 23d from the illuminating direction 24d in order to inspect the color filter edge 23d. That is, it is preferable that at least one of the illuminating directions be opposite another with respect to a surface including the line normal to that principal surface of the substrate on which the color filter has been formed. Light made to shine on and reflected by the color filter edges 23a and 23d is imaged by the sensor (imaging means) 3. That is, in the case shown in FIG. 8, four images are obtained. It should be noted that the angle of illumination is as already explained.

Since the present invention only needs to obtain at least two images, the number of color filter edges to be imaged per pixel may be one. However, in cases where the number of color filter edges to be imaged per pixel is one and the color filter edge has a shape that makes it difficult for unevenness to occur, there is a possibility of overlooking unevenness occurring in other sites. Therefore, the number of color filter edges to be imaged per pixel is preferably two rather than one, more preferably three rather than two, or still more preferably four rather than three. The reason for this is as follows: An increase in the number of different color filter edges to be imaged causes an increase in the number of pieces of information for making a determination, thereby making it possible to detect unevenness with higher accuracy.

The sensor (imaging means) 3 may image reflected light in any imaging direction. However, it is preferable that at least one of the imaging directions be opposite another with respect to a surface including the line normal to that principal surface of the substrate on which the color filter has been formed. In cases where all the imaging directions are on the same side with respect to a surface including the line normal to the principal surface of the substrate, i.e., all the imaging directions are parallel to a direction normal to the principal surface of the substrate, the imaging system is struck by specular reflected light. This may make it difficult to make a difference in luminance among color filter edges.

From the point of view of detecting a difference (i.e., unevenness) in luminance among color filter edges with high accuracy, it is preferable that at least one of the imaging directions be opposite another with respect to a surface including the line normal to that principal surface of the substrate on which the color filter has been formed. Furthermore, in order to detect a difference in luminance among color filter edges with higher accuracy, it is preferable that at least two of the imaging directions be perpendicular to two opposing sides of the black matrix, or it is more preferable that the imaging directions be four directions perpendicular to four sides of the black matrix (hereinafter referred to simply as "four directions").

Unevenness of a color filter edge 23 is a minute change when seen microscopically, and is therefore difficult to detect. Therefore, the whole color filter 10 is macroscopically inspected for abnormality (unevenness) in surface shape of the color filter 10 by calculating a difference in luminance across the whole color filter 10 from shot images different in luminance.

As explained above, FIG. 8 shows a case where the color filter edges 23a to 23d are illuminated from the illumination directions 24a to 24d, respectively. In this case, in order to detect a difference in luminance among the color filter edges 23a to 23d with high accuracy, it is most preferable that the light from the illuminating direction 24a be imaged from the illuminating direction 24b, that the light from the illuminating direction 24b be imaged from the illuminating direction 24a, that the light from the illuminating direction 24c be imaged from the illuminating direction 24d, and that the light from the illuminating direction 24d be imaged from the illuminating direction 24c. In this case, as shown in FIG. 8, the imaging directions are four directions respectively perpendicular to four sides of the black matrix.

It is possible to install a pair of an illumination lamp (illuminating means) 2 and a sensor (imaging means) 3 for each imaging direction. However, the present invention is not limited to this. It is also possible to install only a single pair of an illumination lamp (illuminating means) 2 and a sensor (imaging means) 3.

Figure 9:
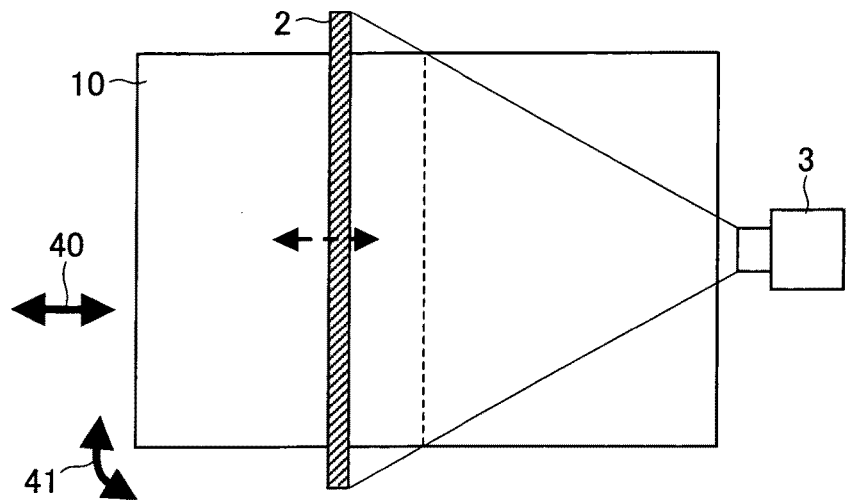
FIG. 9 explains a case where the color filter 10 is imaged from four directions (four directions perpendicular to four sides of a black matrix) with a single pair of a sensor (imaging means) 3 and an illumination lamp (illuminating means) 2.

FIG. 9 explains a case where the color filter 10 is imaged from four directions (four directions perpendicular to four sides of the black matrix) with a single pair of a sensor (imaging means) 3 and an illumination lamp (illuminating means) 2.

First, the illumination lamp (illuminating means) 2 is positioned so that a color filter edge 23 is illuminated and imaged. Next, the color filter 10 is scanned in the substrate-scanning directions 40 and imaged with the sensor (imaging means) 3. Then, the position of the illumination lamp (illuminating means) 2 is adjusted by subjecting the color filter 10 to a 90-degree rotation 41. Next, the color filter 10 is scanned in the substrate-scanning directions 40 and imaged with the sensor (imaging means) 3. Similarly, the color filter 10 is subjected to a 90-degree rotation 41. Thus obtained are images taken from all the four directions. In this way, even a single pair of an illumination lamp (illuminating means) 2 and a sensor (imaging means) 3 make it possible to obtain images taken from all the four directions.

Although FIG. 9 shows an arrangement in which the color filter 10 is rotated, there may be an arrangement in which the color filter 10 is not rotated but only scanned and the illumination lamp (illuminating means) 2 and the sensor (imaging means) 3 are rotated 90 degree every time the color filter 10 is scanned in one direction.

Figure 10:
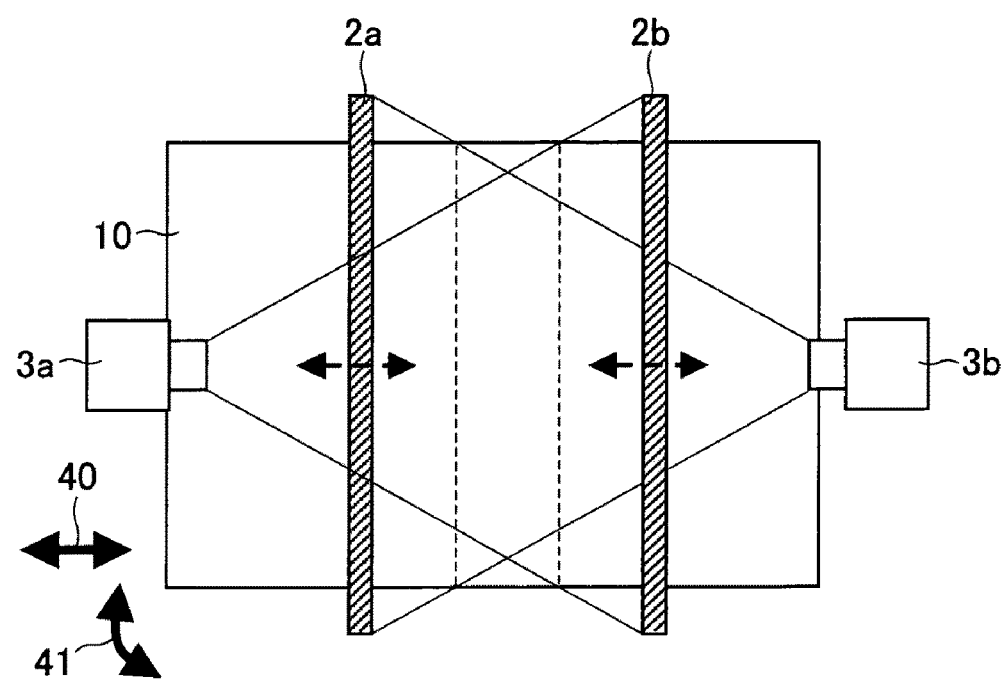
FIG. 10 shows the disposition of two sets of a sensor (imaging means) 3, an illumination lamp (illuminating means) 2, and an illumination-lamp driving stage 4.

FIG. 10 shows the disposition of two sets of a sensor (imaging means) 3, an illumination lamp (illuminating means) 2, and an illumination-lamp driving stage 4. It takes inspection time to subject a color filter 10 or a pair of an illumination lamp (illuminating means) 2 and a sensor (imaging means) 3 to four 90-degree rotations in order to obtain images taken from four directions perpendicular to four sides of the black matrix 20 when the color filter 10 is observed from a direction normal to the principal surface of the substrate 100.

In view of this, in order that images taken from two directions are obtained each time the substrate is scanned, a pair of a sensor 3a and an illumination lamp 2a and a pair of a sensor 3b and an illumination lamp 2b are installed so as to be positioned perpendicularly to two opposing sides of the color filter 10 (two opposing sides of the black matrix), respectively. With this arrangement, images taken from two directions can be obtained each time the substrate is scanned, so that images taken from four directions (four directions perpendicular to four sides of the black matrix) can be obtained simply by scanning the color filter 10 again after rotating it 90 degrees. This effectively makes it possible to shorten time required for measurement and to reduce initial investment in facilities.

In cases where two pairs of an illumination lamp (illuminating means) 2 and a sensor (imaging means) 3 are mounted, the pair of the sensor 3a and the illumination lamp 2a and the pair of the sensor 3b and the illumination lamp 2b only need to be installed, as described above, so as to be positioned perpendicularly to two opposing sides of the color filter 10 (two opposing sides of the black matrix). However, it is more preferable that each of the pair of the sensor 3a and the illumination lamp 2a and the pair of the sensor 3b and the illumination lamp 2b be disposed at equal angles to a line normal to a tangent passing through a point of inflection of the color filter edge. If the angle of incidence and the angle of reflection are at equal angles to a line normal to a tangent passing through a point of inflection of the color filter edge 23, the sensor (imaging means) 3 is prevented from being struck by the light reflected by the pixel central part 22 of the color filter 10, so that the light reflected by the color filter edge 23 can be efficiently detected. Therefore, the accuracy of unevenness detection can be improved by disposing a sensor (imaging means) 3 and an illumination lamp (illuminating means) 2 at equal angles to a line normal to a tangent passing through a point of inflection of the color filter edge, i.e., in positions corresponding to the angle of incidence and the angle of reflection.

In the case of use of two or more illumination lamps (illuminating means) 2, it is preferable not to light on the illumination lamps (illuminating means) 2 alternately but to light all the illumination lamps (illuminating means) 2 simultaneously. Simultaneous lighting makes it possible to simultaneously illuminate different color filter edges 23 from different angles, and therefore brings about improvement in inspection efficiency.

Further, in the case of use of two or more sensors (imaging means) 3, the sensors (imaging means) 3 take images not alternately but simultaneously, because the present invention varies in imaging positions according to directions in which the substrate is scanned.

Figure 11:
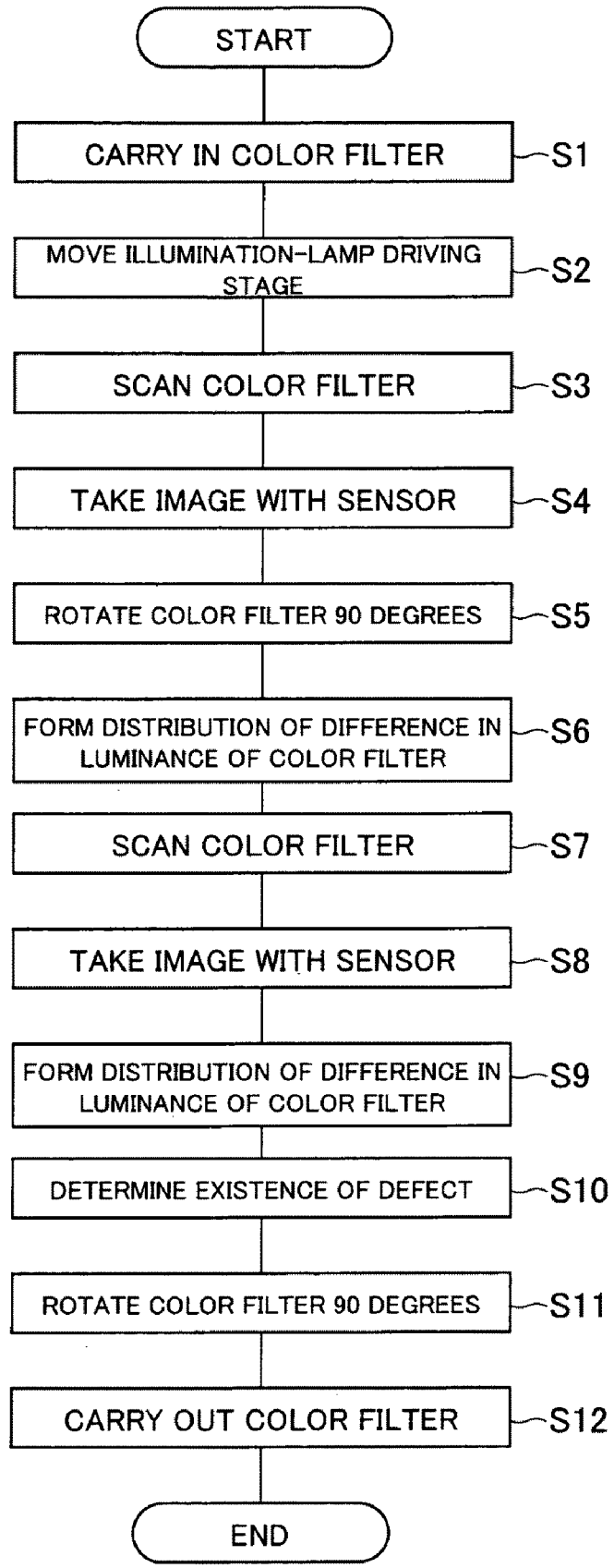
FIG. 11 is a flow chart showing the flow of a process by which the color filter inspection apparatus 1 inspects a color filter.

In the following, the flow of a process by which the color filter inspection apparatus 1 thus arranged inspects a color filter will be described with reference to a flow chart shown in FIG. 11. The following describes the flow of a color filter inspection process that is performed by two sets of a sensor (imaging means) 3, an illumination lamp (illuminating means) 2, and an illumination-lamp driving stage 4.

Prior to the performance of an inspection process, data on each position of the illumination-lamp driving stage 5 is saved as model information on the storage section 7. The data is obtained through experimental measurement of perfect positional data on the illumination-lamp driving stage 5 for obtaining a direction from which each image is taken. The experimental measurement is performed with use of an even reference sample identical in model (arranged identically in pixel size, color filter member, quantity, and the like) to the color filter 10, which is to be inspected. The unevenness of the color filter 10, which is to be inspected, is measured by using the reference sample as a background.

First, a substrate conveying section (not shown) carries the color filter 10 in the substrate driving stage 4 provided in the color filter inspection apparatus 1 (S1). The substrate conveying section transmits, to the control device 6, model information on the color filter 10 thus carried in. The control device 6 takes out, from the storage section 7, that positional data information on the illumination-lamp driving stage 5 which corresponds to the model information on the color filter 10 thus carried in.

Next, each of the illumination-lamp driving stages 5 is moved in accordance with the positional data information taken out from the storage section 7 (S2). For the purpose of obtaining, in a single scan, images taken from positions perpendicular to two opposing sides of the color filter 10 (two opposing sides of the black matrix), each of the illumination-lamp driving stages 5 is moved in accordance with positional data on two directions.

Next, each of the illumination lamps (illuminating means) 2 illuminates the color filter 10 and starts to scan the color filter 10 placed on the substrate driving stage 4 (S3: illuminating step). Then, when the color filter 10 placed on the substrate driving stage 4 comes to an imaging starting position where a sensor (imaging means) 3 starts imaging, the sensor (imaging means) 3 starts imaging (S4: imaging step). Each sensor (imaging means) 3 differs in imaging starting position from the other. Therefore, the sensor (imaging means) 3 starts imaging in the corresponding imaging starting position.

After completion of the scan of the color filter 10, the color filter 10 is rotated 90 degrees (S5). At the same time, the images taken with the sensors (imaging means) 3 form a two-dimensional image at the image processing section (shot-image information analyzing means) 9, which then measures a distribution of difference in luminance of the color filter 10 by calculating a difference in luminance within the color filter 10 (S6: shot-image information analyzing step). The control device 6 takes out, from the storage section 7, that positional data on the illumination-lamp driving stage 5 which corresponds to the direction rotated 90 degrees. The illumination-lamp driving stage 5 is moved in accordance with the positional data information. Since these processes can be concurrently performed, it becomes possible to shorten inspection time.

Next, the color filter 10 is scanned so as to be imaged from the direction rotated 90 degrees (S7: illuminating step 7).

Next, when the color filter 10 placed on the substrate driving stage 4 comes to a line-sensor imaging starting position, the sensor (imaging means) 3 starts imaging (S8: imaging step). Each sensor (imaging means) 3 differs in imaging starting position from the other. Therefore, the sensor (imaging means) 3 starts imaging in the corresponding imaging starting position.

After completion of the scan of the color filter 10 and completion of the imaging by each sensor (imaging means) 3, the image processing section (shot-image information analyzing means) 9 forms a two-dimensional image and forms a distribution of difference in luminance of the color filter 10 (S9: shot-image information analyzing step). Distributions of difference in luminance of the color filter 10 in the four directions are obtained, and the existence of a defect is determined by taking out a luminance difference threshold for a defect from the storage section 7 (S10: unevenness determining step). An optimum luminance difference threshold for a defect can be obtained through a database built in advance by investigating a relationship between an inspection value and a defect caused when a liquid crystal panel is manufactured.

Figure 12:
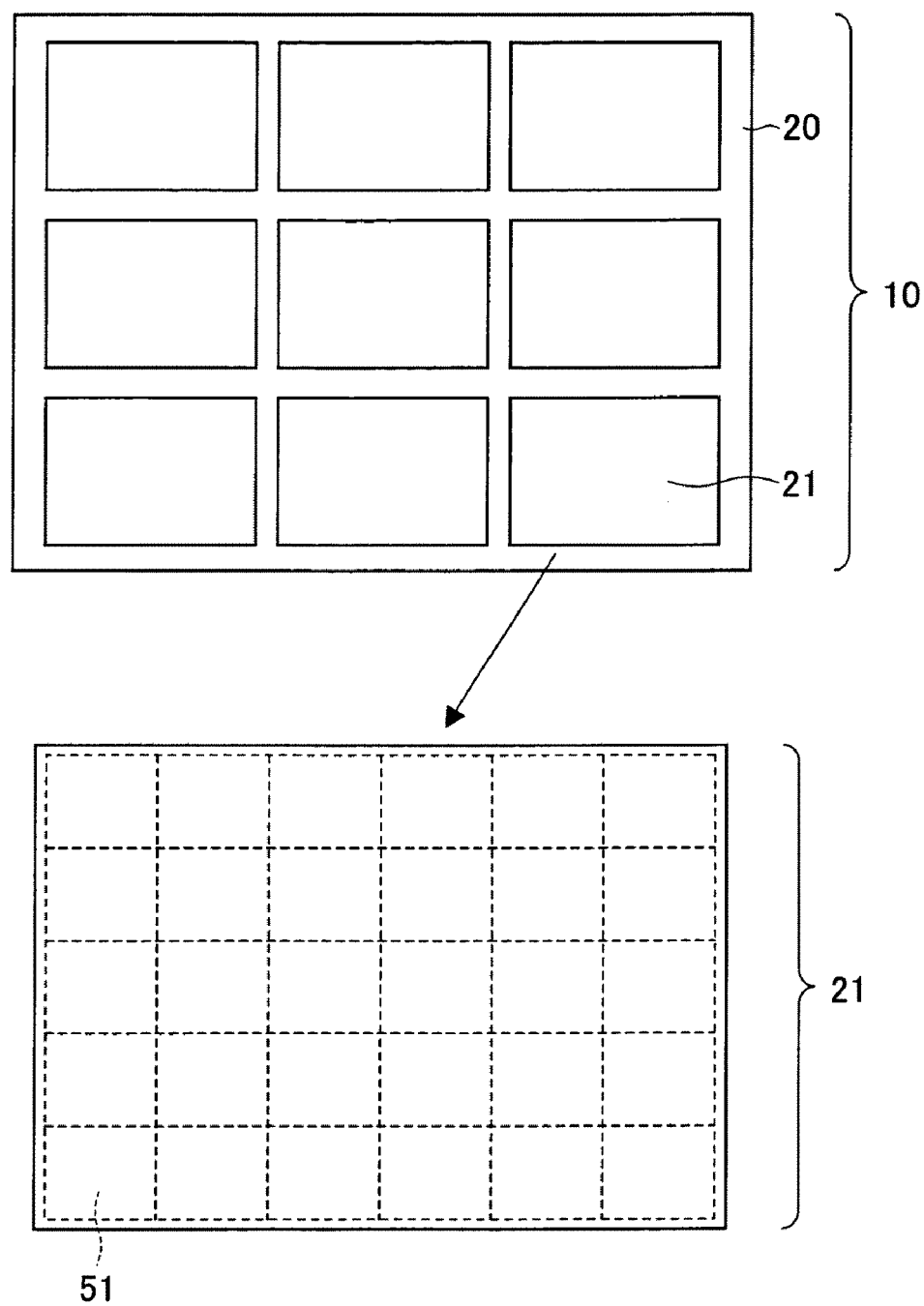
FIG. 12 is an explanatory diagram explaining a specific method for obtaining a luminance difference distribution and determining the existence of a defect.

In the following, a specific method for obtaining a luminance difference distribution and determining the existence of a defect will be described with reference to FIG. 12. As shown in FIG. 12, the color filter 10 can be divided into pixels 21 for making a plurality of panels on a single substrate 100. It is only necessary to determine a difference in luminance for each pixel 21 and to divide a shot image luminance distribution regions 51 for calculating a distribution of difference in luminance for each pixel 21.

Each of the luminance distribution regions 51 can be automatically set in accordance with information, such as the size of the luminance distribution region 51, which is set in advance in the storage section 7, because the number, size, and location of pixels 21, are known from such substrate information on the color filter 10 as obtained in S1. The defect determination section (unevenness determining means) 13 can obtain a luminance distribution for each pixel 21 by calculating the average luminance value of each luminance distribution region 51.

Further, since it is possible to obtain a luminance distribution for each pixel 21 from images obtained by imaging the color filter 10 from the four directions, the defect determination section (unevenness determining means) 13 calculates the difference between the minimum and maximum luminance values for each direction and has it displayed by the monitor 8. The way in which luminance is distributed in each direction is also displayed by the monitor 8 so as to be known to the apparatus administrator (operator).

Furthermore, the defect determination section (unevenness determining means) 13 takes out, from the storage section 7, a luminance difference distribution threshold for determining the existence of a predetermined defect and judges whether differences in luminance distribution in the four directions are higher than the threshold, thereby automatically judging between conforming and defective products. The defect determination section (unevenness determining means) 13 determines the existence of a defect in the whole color filter 10 after determining the existence of a defect in each pixel 21. It is also possible to judge the color filter 10 as a conforming or defective product by presetting the percentage of conforming products in units of pixel.

Next, for the purpose of carrying out the substrate after orienting the substrate in the same direction as it was in when carried in, the color filter 10 is rotated 90 degrees in a direction opposite the direction in which it was rotated in S5 (S11). In so doing, it is possible to shorten inspection time by concurrently performing a process according to the defect determination of S8.

Finally, the color filter 10 is carried out from the color filter inspection apparatus 1 (S12). That is, the substrate drive control section 11 controls the substrate driving stage 4 so that the color filter 10 is ready to be carried out, and then the substrate conveying section carries out the color filter 10.

As described above, the color filter inspection apparatus 1 can automatically conduct a series of inspections of color filters 10 and can easily determine, from images obtained by imaging the substrate from the four directions, whether the color filters 10 are conforming or defective products (existence of defects). This makes it possible that when there occurs defective products (especially in large numbers), an apparatus abnormality in the drying step at the time of formation of color filters is immediately reported to a manufacturing apparatus responsible for the drying step, and then to the operator. Further, the transmission of defect inspection information on the substrate to the factory's information system makes it possible to send only conforming products to a subsequent step and thereby bring about improvement in yield at the time of manufacture of liquid crystal panels. Further, it also becomes possible that if there occur a large number of defective products at the time of production of color filters, the drying-step apparatus is provided with feedback.

The color filter manufacturing method according to the present invention supplies, to an inspection step and a step subsequent thereto, only a color filter judged as a conforming product by the color filter inspection method according to the present invention, and can therefore bring about improvement in yield of color filters.

FIG. 18 is a flow chart showing, as a typical example of a color filter manufacturing step, a manufacturing step based on a pigment dispersion method. Of course, the manufacturing step may be based on a method other than the pigment dispersion method such as a staining method, a printing method, or an electrodeposition method. A color filter manufacturing step to which the color filter manufacturing method according to the present invention can be applied is not limited to those steps shown in FIG. 18. The color filter manufacturing method according to the present invention can be applied to any step in a color filter manufacturing step. In the following, a case where the color filter manufacturing method according to the present invention is applied to a color filter manufacturing step will be described with reference to FIG. 18.

The color filter manufacturing step shown in FIG. 18 includes the step S201 of carrying in a substrate, the step S202 of forming a black matrix (BM), the step S203 of forming a colored pattern, the step S204 of forming a protective film, the step S205 of forming a transparent electrode film, the step S206 of inspection, and the step S207 of carrying out a color filter. The substrate is finished as a color filter via these steps. FIG. 18 shows, by way of example, that the step S206 is performed after completion of the step S205. However, the present invention is not limited to this. The step S206 can be performed at any step in the color filter manufacturing step.

For example, unevenness having occurred up to resist application can be detected by performing the color filter inspection method according to the present invention as the step S206 after resist application in the step S203. For example, if the substrate has unevenness in surface condition of a layer contacted by the applied liquid, there appears a difference in contact angle of the applied layer between an uneven portion and an even portion, and this difference causes a difference in shape of the applied layer. Therefore, the difference in shape can be detected as unevenness. Thus, the unevenness in surface condition of a layer contacted by the applied liquid can be detected, for example, by performing the step S206 after resist application. This makes it possible to supply only a conforming product to the subsequent step.

Further, the unevenness having occurred up to resist application can be detected, for example, by performing the step S206 after resist application in the step S202. That is, if unevenness has occurred in the BM up to resist application, the unevenness causes a difference in width of the BM between an edge and a central part after resist application. Therefore, the unevenness having occurred in the BM can be detected by performing the step S206 after resist application. This makes it possible to supply only a conforming product to the subsequent step.

Further, for example, from the point of view of achieving uniform resist application, it is preferable that the resist temperature be held constant. However, in cases where the temperature cannot be held constant during resist application for some reason, a change in amount applied causes unevenness. Even in such a case, unevenness accompanying such a change in resist temperature can be detected by performing the step S206 after resist application. This makes it possible to supply only a conforming product to the subsequent step.

As exemplified above, the color filter manufacturing method according to the present invention performs the color filter inspection method according to the present invention in the step S206 and supplies, to an inspection step and a step subsequent thereto, only a color filter judged as a conforming product, thereby preventing an uneven color filter from passing through the inspection step and the step subsequent thereto. This enables improvement in yield of color filters and thereby achieves a reduction in manufacturing cost. It should be noted that the phrase "color filter judged as a conforming product" means not only a finished color filter but also an intermediate product.

Further, in cases where there occurs a color filter judged as a defective product by the color filter inspection method according to the present invention, the color filter manufacturing method according to the present invention notifies a color filter manufacturing apparatus of information on the occurrence of the defective product. Therefore, if there occur a large number of defective products at the time of production of color filters, the color filter manufacturing apparatus can be immediately provided with feedback. This enables a reduction in the rate of occurrence of defective products.

As shown in FIG. 13(a), a color filter inspection apparatus 1a according to another embodiment of the present invention can be arranged such that: a illumination lamp (illuminating means) 2 capable of radiating all-round diffused light is used; the illumination lamp (illuminating means) 2 is mounted on a retractable illumination-lamp driving section 101; and the distance from the color filter 10 to the illumination lamp (illuminating means) 2 can be changed by adjusting the length of the illumination-lamp driving section 101.

(a) of FIG. 13 is a pattern diagram showing a longitudinal section of an optical system of the color filter inspection apparatus 1a. The optical system of the color filter inspection apparatus 1a is constituted by the illumination-lamp driving section 101, the illumination lamp (illuminating means) 2, a unit rotating shaft 102, a unit housing 3, and sensors (imaging means) 3a and 3b.

In (a) of FIG. 13, the illumination-lamp driving section 101 moves up and down to change the distance from the color filter 10 to the illumination lamp (illuminating means) 2. Since the illumination-lamp driving section 101 has a lower end equipped with the illumination lamp (illuminating means) 2, all the color filter edges 23 of the color filter 10 can be illuminated at a predetermined angle by elongating and contracting the illumination-lamp driving section 101 without moving the color filter 10.

In this case, the imaging direction is a direction inclined at 0 degree to a line normal of that principal surface of the substrate on which the color filer has been formed. That is, the angle of reflection of light is in a direction normal to the principal surface of the substrate. In (a) of FIG. 13, the two sensors (imaging means) 3a and 3b are provided so as to be arranged in directions from side to side. This makes it possible to simultaneously image color filter edges 23, illuminated simultaneously, which are positioned differently in the directions from side to side.

In the case of (a) of FIG. 13, the two sensors (imaging means) 3a and 3b are provided. Therefore, for example, after imagining of a color filter edge 23 constituted by a black matrix 20 extending in the directions from side to side and a pixel 21, it is necessary to rotate the unit rotating shaft 102 90 degrees in order to image a color filter edge 23 constituted by a black matrix 20 extending in anteroposterior directions orthogonal to the black matrix 20 extending in the directions from side to side and a pixel 21. However, it is not necessary to rotate the color filter 10.

If four sensors (imaging means) 3 are provided so as to be arranged in the directions from side to side and the anteroposterior directions (four orthogonal directions), there is an increase in the size of the color filter inspection apparatus 1. However, the four sensors (imaging means) 3 make it possible to quickly take images from the four directions without rotating the unit rotating shaft 102 and thereby shorten inspection time.

(b) of FIG. 13 is a perspective view of the color filter inspection apparatus 1a. In (b) of FIG. 13, the portion surrounded by the dotted line indicates a place that is illuminated by a specular refection of illuminating light, and the shaded portion indicates an imaging position to take images in the directions from side to side. The housing 103 occupies a region corresponding to a region occupied by a single pixel 21 of the color filter 10.

As described above, the color filter inspection apparatus 1a is wholly rotatable. Therefore, provision of a single illumination lamp (illuminating means) 2 and a pair of sensors (imaging means) 3a and 3b makes it possible that a color filter edge 23 constituted by a black matrix 20 extending in the directions from side to side and a pixel 21 is imaged at a time from the imaging direction shown in (b) of FIG. 13. Then, a 90-degree rotation of the unit rotating shaft 102 makes it possible to image a color filter edge 23 constituted by a black matrix 20 extending in the anteroposterior directions orthogonal to the black matrix 20 extending in the directions from side to side and a pixel 21.

As shown in (a) of FIG. 14, a color filter inspection apparatus 1b according to another embodiment of the present invention can use, as an illumination lamp (illuminating means) 2, an illumination lamp (illuminating means) 2 that illuminates the color filter 10 partially or in beam form. It should be noted that the word "partially" means not the whole area of the color filter 10 but that area of the color filter 10 which can be illuminated by a line lamp.

(a) of FIG. 14 is a pattern diagram showing a longitudinal section of an optical system of the color filter inspection apparatus 1b.

In this case, the direction of illumination is a direction inclined at 0 degree to a line normal to the principal surface of the substrate, i.e., a direction normal to the principal surface of the substrate, and the light sent to a single imaging position from the direction normal to the principal surface of the substrate and reflected in difference directions is imaged with two sensors (imaging means) 3.

As shown in (a) of FIG. 14, the color filter inspection apparatus 1b is constituted by an illumination lamp (illuminating means) 2, sensors (imaging means) 3a and 3b, a unit housing 103, imaging driving means (guide rails) 104a and 104b, and imaging driving means (for use in angle adjustment) 105a and 105b.

The unit housing 103 fixes the illumination lamp (illuminating means) 2 and the imaging driving means (guide rails) 104a and 104b. The imaging driving means (guide rails) 104a and 104b move the sensors (imaging means) 3a and 3b from side to side via the imaging driving means (for use in angle adjustment) 105a and 105b, respectively.

Further, the imaging driving means (guide rails) 104a and 104b are also arranged so as to be able to move up and down. The imaging driving means (for use in angle adjustment) 105a and 105b fix the sensors (imaging means) 3a and 3b to the imaging driving means (guide rails) 104a and 104b, and make it possible to adjust the angles of the sensors (imaging means) 3a and 3b on the imaging driving means (guide rails) 104a and 104b, respectively. The vertical motions of the imaging driving means (guide rails) 104a and 104b and the movability of the imaging driving means (for use in angle adjustment) 105a and 105b make it possible to adjust the imaging direction at a desired angle matched with the angle of reflection of light.

(b) of FIG. 14 is a perspective view of the color filter inspection apparatus 1b. In (b) of FIG. 14, the portion surrounded by the dotted line indicates a place that is illuminated by a specular refection of illuminating light, and the shaded portion indicates an imaging position to take images in the directions from side to side.

The procedure for imaging a single color filter 10 with the color filter inspection apparatus 1b of the present embodiment will be described with reference to FIGS. 16 and 17. FIG. 16 is a pattern diagram showing the way the color filter 10 is observed, from a direction normal to the principal surface of the substrate, being imaged in directions from side to side. Further, FIG. 17 is a pattern diagram showing the way the color filter 10 is observed, from a direction normal to the principal surface of the substrate, being imaged in anteroposterior directions.

In the following, by way of example for consideration, the color filter 10 is divided into five rows, namely the Ath to Eth rows, as shown in FIG. 16, and divided into four columns, namely the first to fourth columns, as shown in FIG. 17. That is, the following describes a case where the whole color filter 10 is macroscopically inspected by dividing that region of the substrate on which the color filter 10 has been formed and by conducting an inspection for each of the parts into which the region has been divided.

First, as shown in FIG. 16(a), the color filter inspection apparatus 1 is moved from left to right while causing the illumination lamp (illuminating means) 2 (not shown in FIG. 16) to illuminate a color filter edge 23 present in the Ath row at an angle inclined at 0 degree to a line normal to the principal surface of the substrate and causing the sensors (imaging means) 3a and 3b to image reflected light. After the Ath row is imaged, the color filter 10 is shifted frontward by the substrate driving stage 4 and then halted.

Next, as shown in FIG. 16(b), the color filter inspection apparatus 1b is moved from right to left while causing the illumination lamp (illuminating means) 2 (not shown in FIG. 16) to radiate light so that the light strikes a color filter edge 23 present in the Bth row at an angle inclined at 0 degree to a line normal to the principal surface of the substrate and imaging the reflected light with the sensors (imaging means) 3a and 3b. After the Bth row is imaged, the color filter is shifted frontward by the substrate driving stage 4 and then halted. Subsequently, illumination and imaging are similarly repeated from the Ath to Eth rows in sequence.

By thus imaging the reflected light with the two sensors (imaging means) 3a and 3b while moving the color filter inspection apparatus 1b from side to side, light reflected in different imaging directions from two or more different color filter edges per pixel can be imaged.

The foregoing has described a case where the color filter 10 is inspected by moving the color filter inspection apparatus 1b from side to side with the color filter 10 fixed. However, the present invention is not limited to this. There may be an arrangement in which the color filter 10 is moved from side to side with the color filter inspection apparatus 1b fixed.

As shown in (a) of FIG. 14, when observed from a direction parallel to the color filter 10, each of the imaging directions is at an angle αL to a direction normal to the principal surface of the substrate. However, when the color filter 10 is observed from a direction normal to that principal surface of the substrate on which the color filter 10 has been formed, the imaging direction is perpendicular to the black matrix 20.

For the purpose of further improving the accuracy of unevenness detection by imaging light reflected by four different color filter edges per pixel in different imaging directions, the color filter 10 is scanned in one direction for each column either after rotating the color filter 10 90 degrees without rotating the color filter inspection apparatus 1b, or after rotating the color filter inspection apparatus 1b 90 degrees without rotating the color filter 10. For example, the color filter 10 is scanned frontward as shown in FIG. 17(a) when the first column is scanned, and the color filter 10 is scanned backward as shown in FIG. 17(b) when the second column is scanned.

In order to conduct inspections without rotating the color filter inspection apparatus 1b or the color filter 10, the color filter inspection apparatus 1b can be arranged so as to include an illumination lamp (illuminating means) and a pair of sensors (imaging means) for use in inspections of color filter edges 23 extending in the directions from side to side and an illumination lamp (illuminating means) and a pair of sensors (imaging means) for use in inspections of color filter edges 23 extending in the anteroposterior directions. That is, the color filter inspection apparatus 1b may include two sets of an illumination lamp (illuminating means) and a pair of sensors (imaging means).

As shown in (a) of FIG. 15, a color filter inspection apparatus 1c according to another embodiment of the present invention include two illumination lamps (illuminating means) 2 and two sensors (imaging means) 3. The two illumination lamps (illuminating means) 2 illuminate the color filter 10 from different illuminating directions, and the two sensors (imaging means) 3 image reflected light from different imaging directions. (a) of FIG. 15 is a pattern diagram showing a longitudinal section of an optical system of the color filter inspection apparatus 1c.

As shown in (a) of FIG. 15, the optical system of the color filter inspection apparatus 1c according to the present embodiment is constituted by illumination lamps (illuminating means) 2a and 2b, sensors (imaging means) 3a and 3b, illumination-lamp driving means 101a and 101b, a unit rotating shaft 103, and imaging driving means (for use in angle adjustment) 105a and 105b.

The illumination-lamp driving means 101a and 101b can adjust the angles of the illumination lamps (illuminating means) 2a and 2b so that the illumination lamps (illuminating means) 2a and 2b are inclined at angles $\theta R_1$ and $\theta L_1$ to a line normal to the principal surface of the substrate of the color filter 10, respectively. The imaging driving means (for use in angle adjustment) 105a and 105b can adjust the angles of the sensors (imaging means) 3a and 3b so that the sensors (imaging means) 3a and 3b are inclined at angles $\theta L_2$ and $\theta R_2$ to the line normal to the principal surface of the substrate of the color filter 10, respectively.

It should be noted here that $\theta L_2$ and $\theta R_2$ are equal angles and $\theta L_1$ and $\theta R_1$ are equal angles. This makes it possible to inspect different color filter edges under the same conditions. It should be noted that when the color filter is seen macroscopically, each of the angles $\theta R_1$, $\theta R_2$, $\theta L_1$, and $\theta L_2$ is an angle that is determined as an angle formed with a line normal to the principal surface of the substrate.

This makes it possible to illuminate two or more different color filter edges per pixel from different illuminating directions and to image light reflected by two or more different color filter edges per pixel in different imaging directions.

(b) of FIG. 15 is a perspective view of the color filter inspection apparatus 1c. In (b) of FIG. 15, the portion surrounded by the dotted line indicates a place that is illuminated by a specular refection of illuminating light, and the shaded portion indicates an imaging position to take images in the directions from side to side.

The procedure for imaging a single color filter 10 with the color filter inspection apparatus 1c of the present embodiment will be described with reference to FIGS. 16 and 17 in the same manner as the color filter inspection apparatus 1b.

First, as shown in FIG. 16(a), the color filter inspection apparatus 1c is moved from left to right while causing the illumination lamps (illuminating means) 2a and 2b (not shown in FIG. 16) to illuminate a color filter edge 23 present in the Ath row at angles $\theta R_1$ and $\theta L_1$, respectively, and causing the sensors (imaging means) 3a and 3b to image reflected light inclined at angles $\theta L_2$ and $\theta R_2$, respectively. After the Ath row is imaged, the color filter is shifted frontward by the substrate driving stage 4 and then halted.

Next, as shown in FIG. 16(b), the color filter inspection apparatus 1c is moved from right to left while causing the illumination lamps (illuminating means) 2a and 2b (not shown in FIG. 16) to illuminate a color filter edge 23 present in the Bth row at angles $\theta R_1$ and $\theta L_1$, respectively, and causing the sensors (imaging means) 3a and 3b to image reflected light. After the Bth row is imaged, the color filter is shifted frontward by the substrate driving stage 4 and then halted. Subsequently, illumination and imaging are similarly repeated from the Ath to Eth rows in sequence.

The foregoing has described a case where the color filter 10 is inspected by moving the color filter inspection apparatus 1c from side to side with the color filter 10 fixed. However, the present invention is not limited to this. There may be an arrangement in which the color filter 10 is moved from side to side with the color filter inspection apparatus 1c fixed.

For the purpose of further improving the accuracy of unevenness detection by imaging light reflected by four different color filter edges per pixel in different imaging directions, the color filter 10 is scanned in one direction for each column either after rotating the color filter 10 90 degrees without rotating the color filter inspection apparatus 1c, or after rotating the color filter inspection apparatus 1c 90 degrees without rotating the color filter 10. For example, the color filter 10 is scanned backward as shown in FIG. 17(a) when the first column is scanned, and the color filter 10 is scanned frontward when the second column is scanned.

In (a) of FIG. 15, the pair of the sensor 3a and the illumination lamp 2a and the pair of the sensor 3b and the illumination lamp 2b are installed so as to be positioned perpendicularly to two opposing right and left sides of the color filter 10, respectively. However, there may be an arrangement, further having two pairs of an illumination lamp (illuminating means) 2 and a sensor (imaging means) 3 provided respectively on the front and back sides shown in (b) of FIG. 15, for performing illumination and imaging with use of a total of four pairs of an illumination lamp (illuminating means) 2 and a sensor (imaging means) 3. This makes it unnecessary to rotate the color filer 10 or the color filter inspection apparatus 1c, and therefore shortens inspection time. In the case of thus performing illumination and imaging with use of a total of four pairs of an illumination lamp (illuminating means) 2 and a sensor (imaging means) 3, an accurate inspection is made impossible by a tangle of light when illumination and imaging in the directions from side to side and illumination and imaging in the anteroposterior directions are performed simultaneously. Therefore, the system for use in imaging in the anteroposterior directions is halted at the time of imaging in the directions from side to side, and the system for use in imaging in the directions from side to side is halted at the time of imaging in the anteroposterior directions.

As described above, a color filter inspection method according to the present invention is a method for inspecting, for unevenness, a color filter in which each pixel is surrounded by a black matrix, the method including: an illuminating step of illuminating a color filter edge at an angle of incidence inclined at not less than 0 degree to less than (90+α) degrees to a line normal to that principal surface of a substrate on which the color filter has been formed or at an angle of incidence inclined at not less than 0 degree to less than (90−α) degrees to the line normal to the principal surface of the substrate, the color filer edge containing a boundary between the pixel and the black matrix, a being an average degree of inclination of the color filter edge that is not less than 0 degree to less than 90 degrees; an imaging step of taking at least two images of light reflected by the color filter edge at an angle of reflection, different from the angle of incidence, which is not less than 0 degree to less than (90−α) degrees when the angle of incidence is not less than 0 degree to less than (90+α) degrees or is not less than 0 degree to less than (90+α) degrees when the angle of incidence is not less than 0 degree to less than (90−α) degrees; a shot-image information analyzing step of calculating a difference in luminance within the color filter in accordance with the images thus taken; and an unevenness determining step of determining the existence of unevenness of the color filter from the difference in luminance.

Further, as described above, a color filter inspection apparatus according to the present invention is an apparatus for inspecting, for unevenness, a color filter in which each pixel is surrounded by a black matrix, the apparatus including: illuminating means for illuminating a color filter edge at an angle of incidence inclined at not less than 0 degree to less than (90+α) degrees to a line normal to that principal surface of a substrate on which the color filter has been formed or at an angle of incidence inclined at not less than 0 degree to less than (90−α) degrees to the line normal to the principal surface of the substrate, the color filer edge containing a boundary between the pixel and the black matrix, a being an average degree of inclination of the color filter edge that is not less than 0 degree to less than 90 degrees; imaging means for taking at least two images of light reflected by the color filter edge at an angle of reflection, different from the angle of incidence, which is not less than 0 degree to less than (90−α) degrees when the angle of incidence is not less than 0 degree to less than (90+α) degrees or is not less than 0 degree to less than (90+α) degrees when the angle of incidence is not less than 0 degree to less than (90−α) degrees; shot-image information analyzing means for calculating a difference in luminance within the color filter in accordance with the images thus taken; and unevenness determining means for determining the existence of unevenness of the color filter from the difference in luminance.

This results in illumination of a color filter edge at an appropriate angle, taking of at least two images, and determination of the existence of unevenness from a difference in luminance within the color filter in accordance with the images thus taken. This brings about an effect of being able to highly accurately detect unevenness occurring from a minute change in surface shape that is caused in a color filter manufacturing step such as a drying step. Further, this brings about an effect of being able to macroscopically inspect a color filter for unevenness over a wide range.

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

INDUSTRIAL APPLICABILITY

As described above, the present invention illuminates at least two color filter edges per pixel at appropriate angles, takes at least two images, and determines the existence of unevenness from a difference in luminance within the color filter in accordance with the images thus taken, thereby making it possible to highly accurately detect unevenness occurring from a minute change in surface shape that is caused in a step of drying the color filter. Therefore, the present invention can be suitably used in particular to inspect, for unevenness, a substrate in which undulations formed with use of an ink-jet method are arranged regularly, and can be used as means for controlling a color filter manufacturing step.

The invention claimed is:

1. A method for inspecting, for unevenness, a color filter in which each pixel is surrounded by a black matrix, the method comprising:

an illuminating step of illuminating a color filter edge at an angle of incidence inclined at not less than 0 degree to less than (90+α) degrees to a line normal to that principal surface of a substrate on which the color filter has been formed or at an angle of incidence inclined at not less than 0 degree to less than (90−α) degrees to the line normal to the principal surface of the substrate, the color filer edge containing a boundary between the pixel and the black matrix, α being an average degree of inclination of the color filter edge that is not less than 0 degree to less than 90 degrees;

an imaging step of taking at least two images of light reflected by the color filter edge at an angle of reflection, different from the angle of incidence, which is not less than 0 degree to less than (90−α) degrees when the angle of incidence is not less than 0 degree to less than (90+α) degrees or is not less than 0 degree to less than (90+α) degrees when the angle of incidence is not less than 0 degree to less than (90−α) degrees;

a shot-image information analyzing step of calculating a difference in luminance within the color filter in accordance with the images thus taken; and an unevenness determining step of determining the existence of unevenness of the color filter from the difference in luminance.

2. The method as set forth in claim 1, wherein the illuminating step is a step of illuminating two or more different color filter edges per pixel from different illuminating directions at least one of which is opposite another with respect to a surface including the line normal to that principal surface of the substrate on which the color filter has been formed.

3. The method as set forth in claim 1, wherein the imaging step is a step of imaging light reflected by the two or more different color filter edges per pixel in different imaging directions at least one of which is opposite another with respect to a surface including the line normal to that principal surface of the substrate on which the color filter has been formed.

4. The method as set forth in claim 3, wherein the angle of incidence and the angle of reflection are inclined at more than 0 degree.

5. The method as set forth in claim 3, wherein the angle of incidence and the angle of reflection are at equal angles to a line normal to a tangent passing through a point of inflection of the color filter edge.

6. The method as set forth in claim 3, wherein at least two of the imaging directions are perpendicular to two opposing sides of the black matrix.

7. The method as set forth in claim 3, wherein the imaging directions are four directions perpendicular to four sides of the black matrix.

8. The method as set forth in claim 3, wherein the illuminating step and the imaging step are performed with use of a pair of illuminating means and a pair of imaging means, respectively, the illuminating means and the imaging means being disposed at equal angles to the line normal to the tangent passing through the point of inflection of the color filter edge.

9. A method for manufacturing a color filter by supplying, to an inspection step and a step subsequent thereto, only a color filter judged as a conforming product by a method as set forth in claim 1.

10. A method for manufacturing a color filter by, when there occurs a color filter judged as a defective product by a method as set forth in claim 1, notifying a color filter manufacturing apparatus of information on the occurrence of the defective product.

11. An apparatus for inspecting, for unevenness, a color filter in which each pixel is surrounded by a black matrix, the apparatus comprising:

illuminating means for illuminating a color filter edge at an angle of incidence inclined at not less than 0 degree to less than (90+α) degrees to a line normal to that principal surface of a substrate on which the color filter has been formed or at an angle of incidence inclined at not less than 0 degree to less than (90−α) degrees to the line normal to the principal surface of the substrate, the color filer edge containing a boundary between the pixel and the black matrix, α being an average degree of inclination of the color filter edge that is not less than 0 degree to less than 90 degrees;

imaging means for taking at least two images of light reflected by the color filter edge at an angle of reflection, different from the angle of incidence, which is not less than 0 degree to less than (90−α) degrees when the angle of incidence is not less than 0 degree to less than (90+α) degrees or is not less than 0 degree to less than (90+α) degrees when the angle of incidence is not less than 0 degree to less than (90−α) degrees;

shot-image information analyzing means for calculating a difference in luminance within the color filter in accordance with the images thus taken; and unevenness determining means for determining the existence of unevenness of the color filter from the difference in luminance.

\* \* \* \* \*